(12) United States Patent
Schwartz et al.

(10) Patent No.: US 12,139,705 B2
(45) Date of Patent: Nov. 12, 2024

(54) DEEP LEARNING ENABLED SPATIAL OPTICAL BARCODES FOR POOLED LIBRARY SCREENS

(71) Applicant: California Institute of Technology, Pasadena, CA (US)

(72) Inventors: Morgan S. Schwartz, Pasadena, CA (US); David A. Van Valen, Pasadena, CA (US); Edward Pao, San Dimas, CA (US)

(73) Assignee: California Institute of Technology, Pasadena, CA (US)

( * ) Notice: Subject to any disclaimer, the term of this patent is extended or adjusted under 35 U.S.C. 154(b) by 734 days.

(21) Appl. No.: 17/088,594

(22) Filed: Nov. 4, 2020

(65) Prior Publication Data

US 2021/0130810 A1 May 6, 2021

Related U.S. Application Data

(60) Provisional application No. 62/930,343, filed on Nov. 4, 2019.

(51) Int. Cl.
| | | |
|---|---|---|
| *C12N 15/10* | (2006.01) | |
| *C12N 15/11* | (2006.01) | |
| *G06T 7/00* | (2017.01) | |
| *G06V 10/764* | (2022.01) | |
| *G06V 20/69* | (2022.01) | |
| *G16B 40/00* | (2019.01) | |

(52) U.S. Cl.
CPC .......... *C12N 15/1065* (2013.01); *C12N 15/11* (2013.01); *G06T 7/0012* (2013.01); *G06V 10/764* (2022.01); *G06V 20/695* (2022.01); *G06V 20/698* (2022.01); *G16B 40/00* (2019.02); *C12N 2310/20* (2017.05); *G06T 2207/20081* (2013.01); *G06T 2207/30024* (2013.01); *G06T 2207/30072* (2013.01)

(58) Field of Classification Search
None
See application file for complete search history.

(56) References Cited

U.S. PATENT DOCUMENTS

| | | | | |
|---|---|---|---|---|
| 2018/0320226 A1* | 11/2018 | Church | .................. | C12N 15/11 |
| 2019/0177718 A1* | 6/2019 | Church | ................ | C12Q 1/6869 |
| 2019/0247517 A1* | 8/2019 | Brooks | ................ | C12N 15/113 |
| 2020/0364857 A1 | 11/2020 | Moen et al. | | |

FOREIGN PATENT DOCUMENTS

| | | |
|---|---|---|
| WO | WO2017/075265 | 5/2017 |
| WO | WO2017/075294 | 5/2017 |
| WO | WO-2019113499 A1 * | 6/2019 ......... C12N 15/1079 |

OTHER PUBLICATIONS

Lima FM, Souza RT, Santori FR, Santos MF, Cortez DR, et al. (2013) Interclonal Variations in the Molecular Karyotype of Trypanosoma cruzi: Chromosome Rearrangements in a Single Cell-Derived Clone of the G Strain. PLOS One 8(5): e63738 (Year: 2013).*
Bannon et al., "DeepCell Kiosk: Scaling deep learning-enabled cellular image analysis with Kubernetes," bioRxiv 2020, in 23 pages. doi: https://doi.org/10.1101/505032.
Bannon et al., "Dynamic allocation of computational resources for deep learning-enabled cellular image analysis with Kubernetes," bioRxiv 2019, in 17 pages. doi: https://www.biorxiv.org/content/10.1101/505032v3.
Burns et al., "Borg, Omega, and Kubernetes," Queue 2016, 14, 70-93.
Chen et al., "Dynamic Imaging of Genomic Loci in Living Human Cells by an Optimized CRISPR/Cas System," Cell 2013, 155, 1479-1491.
Chen et al., "A Barcoding Strategy Enabling Higher-Throughput Library Screening by Microscopy," ACS Synth Biol 2015, in 12 pages.
Chen et al., "μCB-seq: microfluidic cell barcoding and sequencing for high-resolution imaging and sequencing of single cells," Lab on a Chip 2020, 20, 3899-3913.
Cock et al., "Biopython: freely available Python tools for computational molecular biology and bioinformatics," Bioinformatics 2009, 25(11), 1422-1423.
Deng et al., "CASFISH: CRISPR/Cas9-mediated in situ labeling of genomic loci in fixed cells," PNAS 2015, 112(38), 11870-11875.
Dixit et al., "Perturb-Seq: Dissecting Molecular Circuits with Scalable Single-Cell RNA Profiling of Pooled Genetic Screens," Cell 2016, 167, 1853-1866.
Dong et al., "Polycistronic tRNA and CRISPR guide-RNA enables highly efficient multiplexed genome engineering in human cells," Biochemical and Biophysical Research Communications 2016, in 20 pages. doi: 10.1016/j.bbrc.2016.11.129.
Engler et al., "Golden Gate Shuffling: A One-Pot DNA Shuffling Method Based on Type IIs Restriction Enzymes," PLoS One 2009, 4(5), e5553, in 9 pages.
Engler & Marillonnet, "Golden Gate Cloning," DNA Cloning and Assembly Methods 2014, 1116, 119-131.
Feldman et al., "Lentiviral co-packaging mitigates the effects of intermolecular recombination and multiple integrations in pooled genetic screens," bioRxiv 2018, in 6 pages. doi: https://doi.org/10.1101/262121.
Feldman et al., "Optical Pooled Screens in Human Cells," Cell 2019, 179, 787-799.
Gibson et al., "Enzymatic assembly of DNA molecules up to several hundred kilobases," Nature Methods 2009, 6(5), 343-345.

(Continued)

*Primary Examiner* — Nancy J Leith
*Assistant Examiner* — Jessica D Parisi
(74) *Attorney, Agent, or Firm* — Dickinson Wright PLLC

(57) ABSTRACT

Disclosed herein include systems, methods, and compositions for determining perturbations in single cells or performing integrated measurements using, for example, plasmids each comprising (i) a perturbation gRNA with a guide region targeting a chromosome sequence and (ii) barcode gRNAs each with a guide region targeting predetermined spatial region of the genome and zero, one, or more optical detection probe binding sites.

21 Claims, 15 Drawing Sheets

Specification includes a Sequence Listing.

(56) References Cited

OTHER PUBLICATIONS

Hong et al., "Comparison and optimization of CRISPR/dCas9/gRNA genome-labeling systems for live cell imaging," Genome Biology 2018, 19(39), in 10 pages.
International Search Report and Written Opinion dated Feb. 26, 2021 in PCT Patent Application No. PCT/US2020/058759.
Kishi et al., "SABER amplifies FISH: enhanced multiplexed imaging of RNA and DNA in cells and tissues," Nature Methods 2019, in 19 pages.
Knapp et al., "Decoupling tRNA promoter and processing activities enables specific Pol-II Cas9 guide RNA expression," Nature Communications 2019, 10(1490), 1-14.
Lane et al., "Measuring Signaling and RNA-Seq in the Same Cell Links Gene Expression to Dynamic Patterns of NF-κB Activation," Cell Syst 2017, 4(4), 458-469.
Lotfollahi et al., "scGen predicts single-cell perturbation responses," Nature Methods 2019, 16, 715-721.
Lubeck et al., "Single cell in situ RNA profiling by sequential hybridization," Nat Methods 2014, 11(4), 360-361.
Marillonnet & Werner, "Assembly of Multigene Constructs Using Golden Gate Cloning," Glyco-Engineering 2015, 1321, 269-284.
Moen et al., "Accurate cell tracking and lineage construction in live-cell imaging experiments with deep learning," bioRxiv 2019, in 26 pages. doi: http://dx.doi.org/10.1101/803205.
Moen et al., "Deep learning for cellular image analysis," Nature Methods 2019, 16, 1233-1246.
Plesa et al., "Multiplexed gene synthesis in emulsions for exploring protein functional landscapes," Science 2018, 359, 343-347.
Potapov et al., "Optimization of Golden Gate assembly through application of ligation sequence-dependent fidelity and bias profiling," bioRxiv 2018, in 26 pages. doi: https://doi.org/10.1101/322297.
Rubin et al., "Coupled Single-Cell CRISPR Screening and Epigenomic Profiling Reveals Causal Gene Regulatory Networks," Cell 2019, 176, 361-376.
Shalem et al., "High-throughput functional genomics using CRISPR-Cas9," Nat Rev Genet 2015, 16(5), 299-311.
Shao et al., "Long-term dual-color tracking of genomic loci by modified sgRNAs of the CRISPR/Cas9 system," Nucleic Acids Research 2016, 44(9), e86, in 13 pages.
Shechner et al., "CRISPR Display: A modular method for locus-specific targeting of long noncoding RNAs and synthetic RNA devices in vivo," Nat Methods 2015, 12(7), 664-670.
Sidore et al., "DropSynth 2.0: high-fidelity multiplexed gene synthesis in emulsions," Nucleic Acids Research 2020, 48(16), e95, in 7 pages.
Wang et al., "Imaging-based pooled CRISPR screening reveals regulators of lncRNA localization," PNAS 2019, 116(22), 10841-10851.
Waye & Willard, "Human B satellite DNA: Genomic organization and sequence definition of a class of highly repetitive tandem DNA," PNAS 1989, 86, 6250-6254.
Yuan et al., "Scope-Seq: a scalable technology for linking live cell imaging and single-cell RNA sequencing," Genome Biology 2018, 19(227), in 5 pages.
Zhao, "A one-step tRNA-CRISPR system for genome-wide genetic interaction mapping in mammalian cells," Scientific Reports 2019, 9(14499), in 10 pages.

\* cited by examiner

FIG. 4B1

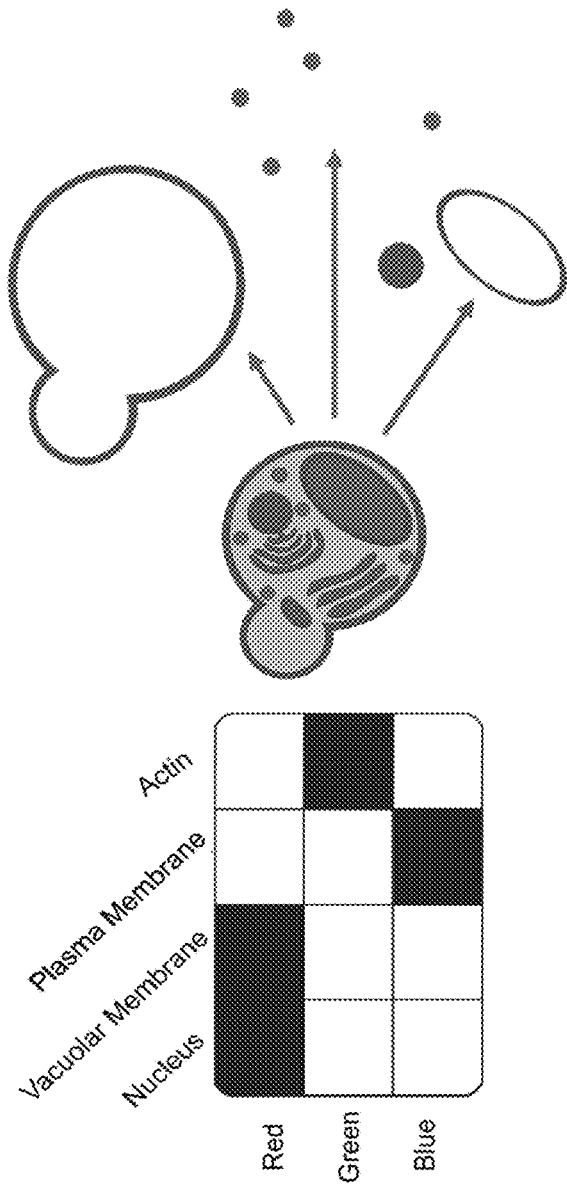
FIG. 4B2

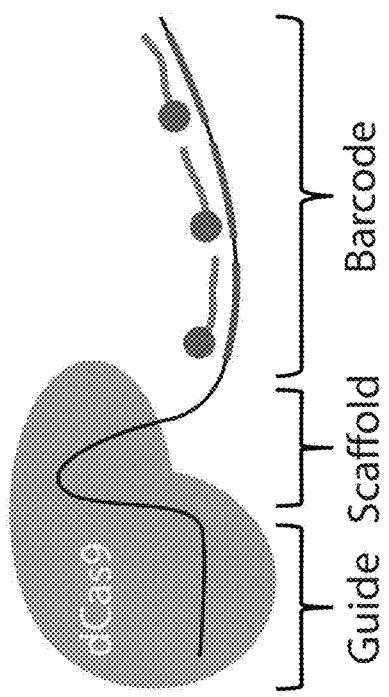
FIG. 8A
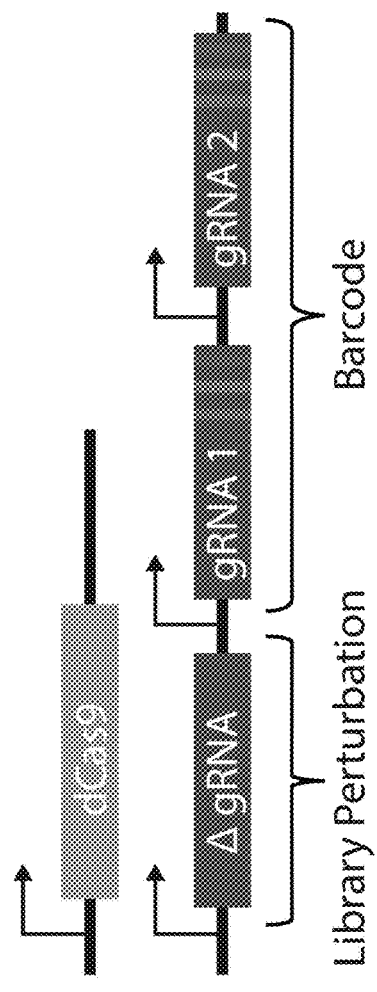
FIG. 8F
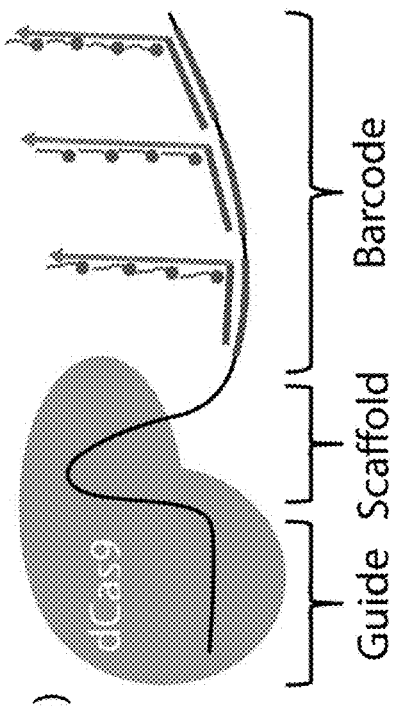
FIG. 8B1
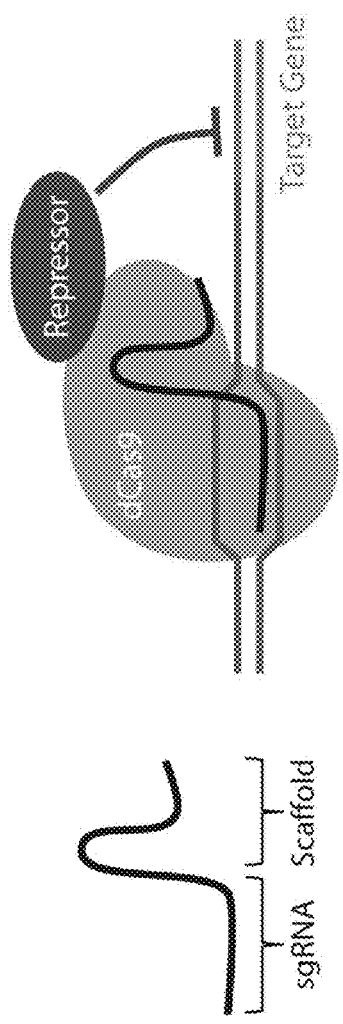
FIG. 8B2

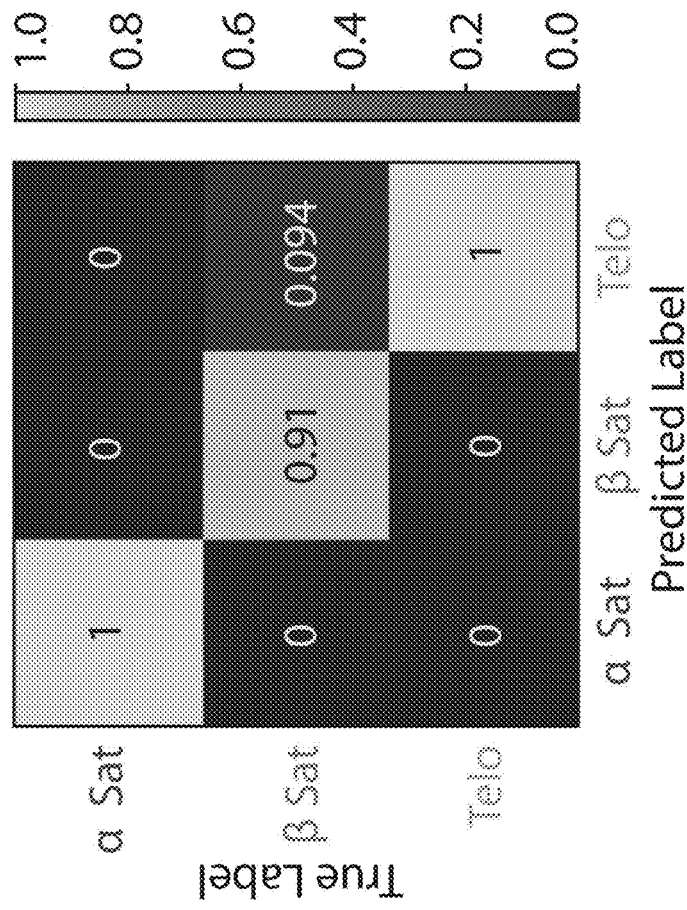
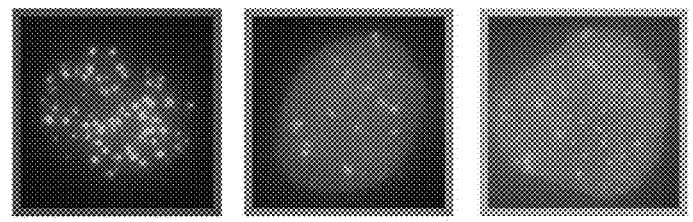
FIG. 8C  FIG. 8D  FIG. 8E

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
gaatctgcaa gtggatatt                                              19

<210> SEQ ID NO 2
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 2
aggtgatgta actcttgtct                                              20

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
gttagggtta gggttagggt ta                                           22
```

DEEP LEARNING ENABLED SPATIAL OPTICAL BARCODES FOR POOLED LIBRARY SCREENS

CROSS-REFERENCE TO RELATED APPLICATIONS

This application claims the benefit of priority to U.S. Patent Application No. 62/930,343, filed on Nov. 4, 2019, the content of which is incorporated herein by reference in its entirety.

REFERENCE TO SEQUENCE LISTING

The present application is being filed along with a Sequence Listing in electronic format. The Sequence Listing is provided as a file entitled Sequences_Listing_30KJ-302425-US, created Nov. 2, 2020, which is 985 bytes in size. The information in the electronic format of the Sequence Listing is incorporated herein by reference in its entirety.

BACKGROUND

Field

This disclosure relates generally to the field of barcoding, and more particularly to spatial optical barcoding.

Background

Advances in imaging and genomics have enabled a shift away from a population level understanding of living systems towards one at the single-cell level. Advances in machine learning methods and their associated hardware accelerators have kept pace with the need to extract insights from these large, single-cell datasets. There is a need to combine deep learning with spatial genomics to create a scalable technological platform for performing imaging-based integrated measurements.

SUMMARY

Disclosed herein include high-throughput methods for determining (or tracking) perturbations in a plurality of single cells. In some embodiments, a high-throughput method for determining perturbations in a plurality of single cells comprises expressing in each of a plurality of single cells (i) a plurality of guide ribonucleic acids (gRNAs) comprising a perturbation gRNA (ΔgRNA) and one or more barcode gRNAs (also referred to herein as compartment gRNAs). The barcode gRNAs each can comprise a barcode region comprising zero, one, or more optical detection probe binding sites for a plurality of optical detection probes. The method can comprise expressing in each of the plurality of single cells (ii) a dead CRISPR associated protein 9 (dCas9). The ΔgRNA can bind to a first dCas9, and the first dCas9 bound to the ΔgRNA can bind to a chromosome sequence of a genome of the single cell, resulting in a perturbation in the single cell. Each of the barcode gRNAs can bind to a second dCas9 and the second dCas9 bound to the barcode gRNA can bind a predetermined spatial region (or compartment or location) of the genome of the single cell. Presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, indicates the ΔgRNA is expressed in the single cell. The method can comprise staining the plurality of single cells with the plurality of optical detection probes. Two optical detection probes of the plurality of optical detection probes can comprise different optical labels and are capable of binding to two optical detection probe binding sites, of the barcode gRNAs expressed in the plurality of single cells, comprising different sequences. Optical detection probes of the plurality of optical barcodes can bind to the optical detection probe binding sites of the barcode gRNAs expressed in the plurality of single cells. The method can comprise imaging the plurality of single cells comprising the optical detection probes bound to the optical detection probe binding sites of the barcode gRNAs expressed in the plurality of single cells to generate a plurality of images. The method can comprise analyzing the plurality of images generated to determine, for each of the plurality of single cells, the combination of optical detection probe binding sites expressed in the single cell and corresponding predetermined spatial regions, thereby determining the perturbation in the single cell.

In some embodiments, each of the plurality of gRNAs comprises from 5' to 3' a guide region (or spacer region) and a scaffold region. The barcode region can be on 3' end of the gRNA. The barcode region can be on 5' end of the gRNA. The scaffold region can comprise the barcode region.

In some embodiments, each of the plurality of gRNAs comprises two or more ΔgRNAs. Each of the two or more ΔgRNAs can bind to a first dCas9 and the first dCas9 bound to the ΔgRNA binds to a chromosome sequence of the genome of the single cell, resulting in a perturbation in the single cell. In some embodiments, the chromosome sequence of the genome of the single cell the first dCas9 bound to the ΔgRNA binds to is predetermined by a guide region of the ΔgRNA. The chromosome sequence of the genome of the single cell the first dCas9 bound to the ΔgRNA binds to can be a reverse complement of a sequence of the guide region of the ΔgRNA. In some embodiments, the chromosome sequence of the genome of the single cell comprises a gene of interest, or a subsequence thereof. In some embodiments, the chromosome sequence of the genome of the single cell comprises a promoter of a gene of interest, or a subsequence thereof.

In some embodiments, the plurality of gRNAs comprises three or more barcode gRNAs. In some embodiments, the predetermined spatial region (or compartment or location) of the genome of the single cell comprises a repetitive region of the genome of the single cell. The predetermined spatial region of the genome of the single cell can comprise a repetitive region of each chromosome of the genome of the single cell. The predetermined spatial region of the genome of the single cell can comprise a telomere, an alpha satellite, a beta satellite of each chromosome of the genome of the single cell. In some embodiments, the predetermined spatial region of the genome of the single cell that the second dCas9 bound to the barcode gRNA binds to is predetermined by a guide region of the barcode gRNA. The predetermined spatial region of the genome of the single cell and/or the guide region of the barcode gRNA can comprise a sequence of 5'-GAATCTGCAAGTGGATATT-3' (SEQ ID NO: 1), 5'-AGGTGATGTAACTCTTGTCT-3' (SEQ ID NO: 2), 5'-GTTAGGGTTAGGGTTAGGGTTA-3' (SEQ ID NO: 3), a reverse complement of any of the proceeding, or a combination thereof.

In some embodiments, the barcode region of a barcode gRNA comprises at least three optical detection probe binding sites. In some embodiments, the barcode region of a barcode gRNA comprises presence or absence of each of at least three possible optical detection probe binding sites. In some embodiments, a combination of an optical detection probe binding site expressed in each of the plurality of single cells and the corresponding predetermined spatial region represents a barcode subunit, and the combination of optical detection probe binding sites expressed in each of the plurality of single cells and the corresponding predetermined spatial regions represents a barcode (or spatial optical barcode) comprising a plurality of barcode subunits (or spatial optical barcode subunits). Each of the plurality of barcode subunits is selected from a plurality of possible barcode subunits. In some embodiments, a number of the plurality of possible barcode subunits is (a number of the optical detection probe binding sites of the barcode region in each of the barcode gRNAs)×(a number of the barcode gRNAs) or (a maximum number of the optical detection probe binding sites of the barcode region in each of the barcode gRNAs)×(a number of the barcode gRNAs).

In some embodiments, a number of possible barcode subunits is (a number of different optical labels of the plurality of optical detection probes)×(a number of the predetermined spatial regions).

In some embodiments, a number of the plurality of possible barcode subunits is about 12 (also referred to herein as a 12-subunit barcode). In some embodiments, the barcode comprises six of the plurality of possible barcode subunits (also referred to herein as a six-subunit barcode).

In some embodiments, the barcode comprises about half of the plurality of possible barcode subunits. In some embodiments, the barcode comprises fewer than all of the plurality of possible barcode subunits. In some embodiments, presence of any of the remaining of the plurality of possible barcode subunits in the barcode indicates an error has occurred. In some embodiments, the method comprises performing error detection using the remaining of the plurality of possible barcode subunits. In some embodiments, a number of barcodes (or the size of the coding space) is $$\frac{(n \times m)!}{\left(\frac{n \times m}{2}\right)! \left(\frac{n \times m}{2}\right)!},$$

where n denotes a number of the optical detection probe binding sites of the barcode region in each of the barcode gRNAs and m denotes a number of the barcode gRNAs, or n denotes a number of different optical labels of the plurality of optical detection probes and m denotes a number of the predetermined spatial regions.

In some embodiments, a number of the plurality of possible barcodes (or the size of the coding space) is $2^{(the\ possible\ number\ of\ barcode\ subunits)}-1$. In some embodiments, the number of barcodes is about 1000. The number of the plurality of possible barcodes can be at least 4000. In some embodiments, a number of the perturbations is about 1000. A number of the perturbations can be at least 4000.

In some embodiments, the plurality of gRNAs is under transcription control of a promoter. Two or more of the plurality of gRNAs can be under control of a promoter. Each of the plurality of gRNAs can under control of a promoter.

In some embodiments, the promoter is a U6 promoter. In some embodiments, the method comprises culturing the plurality of single cells.

In some embodiments, expressing in each of the plurality of single cells the plurality of gRNAs comprises: introducing a plasmid comprising a plurality of gRNAs into each of the plurality of single cells. In some embodiments, the plasmid is a viral vector. The plasmid can be a lentiviral vector. In some embodiments, introducing a plasmid comprising a plurality of gRNAs into each of the plurality of single cells comprises: introducing a plasmid comprising a plurality of gRNAs into each of the plurality of single cells comprises at a multiplicity of infection (MOI) of about 0.5.

In some embodiments, the method comprises assembling a plasmid comprising the plurality of gRNAs expressed in one of the plurality of single cells. Assembling the plasmid can comprise: hybridizing the plurality of gRNAs comprising an identical bead code to a bead comprising the bead code, or a reverse complement thereof; and ligating the plurality of gRNAs to form a plasmid comprising the plurality of gRNAs. In some embodiments, the method comprises assembling a plurality of plasmids each comprising the plurality of gRNAs expressed in one of the plurality of single cells. Assembling the plurality of plasmids can comprise: for each of the pluralities of gRNAs expressed in one of the plurality of single cells, hybridizing the plurality of gRNAs comprising an identical bead code to a bead of a plurality of beads comprising the bead code, or a reverse complement thereof in a first partition, gRNAs of each of the pluralities of gRNAs comprise a different bead code; partitioning each of the plurality of beads into one of a plurality of second partitions; releasing the plurality of gRNAs hybridized to the bead in each of the plurality of second partitions from the bead; and ligating the plurality of gRNAs in each of the plurality second partitions to form a plasmid comprising the plurality of gRNAs in each second partition. Assembling the plurality of plasmids can comprise: for each of the pluralities of gRNAs expressed in one of the plurality of single cells: co-partitioning the barcode gRNAs of the plurality of gRNAs and a unique bead code into a first partition; and generating the plurality of barcode gRNAs comprising the bead code in the first partition; hybridizing each of the pluralities of barcode gRNAs comprising the bead code and a ΔgRNA comprising the bead code to a bead, of a plurality of beads, comprising the bead code, or a reverse complement thereof, in a second partition; partitioning each of the plurality of beads into a third partition of a plurality of third partitions; releasing the barcode gRNAs and the ΔgRNA hybridized to the bead in each of the plurality of third partitions from the bead; and ligating the barcode gRNAs and ΔgRNA in each of the plurality of third partitions to form a plasmid comprising the plurality of gRNAs in the third partition.

In some embodiments, the method comprises: synthesizing the ΔgRNAs comprising the bead codes. In some embodiments, the method comprises: releasing the plurality of plasmids from the plurality of third partitions; purifying the plurality of plasmids; and/or amplifying the plurality of plasmids.

In some embodiments, an identical gRNA is expressed in two or more single cells of the plurality of single cells. In some embodiments, an identical plasmid is introduced into two or more single cells of the plurality of single cells. In some embodiments, the two or more single cells comprise about 150 single cells. In some embodiments, the perturbations in the two or more single cells are different. In some embodiments, the perturbations in the two or more single cells are identical.

In some embodiments, each optical detection probe of the plurality of optical detection probes comprises a different optical label and is capable of binding to a different binding sites, of the barcode gRNAs expressed in the plurality of single cells, comprising a different sequence. In some embodiments, two optical detection probes of the plurality of optical detection probes comprise an identical optical label and are capable of binding to two optical detection probe binding sites, of the barcode gRNAs expressed in the plurality of single cells, comprising different sequences.

In some embodiments, each of the plurality of optical detection probes comprises one of at least three optical labels. In some embodiments, the plurality of optical detection probes comprises a plurality of fluorescent oligonucleotides. In some embodiments, thereby optical detection probes of the plurality of optical barcodes bind directly to the optical detection probe binding sites of the barcode gRNAs expressed in the plurality of single cells. In some embodiments, thereby optical detection probes of the plurality of optical barcodes bind indirectly to the optical detection probe binding sites of the barcode gRNAs expressed in the plurality of single cells via concatemer probes that bind directly to the optical detection probe binding sites of the barcode gRNAs expressed in the plurality of single cells.

In some embodiments, imaging the plurality of single cells comprises imaging the plurality of single cells at 40× magnification to generate the plurality of images. In some embodiments, staining the plurality of single cells with the plurality of optical detection probes comprises one round of staining. In some embodiments, staining the plurality of single cells with the plurality of optical detection probes comprises at most two rounds of staining.

In some embodiments, an image of the plurality of images comprises a single-channel image. In some embodiments, an image of the plurality of images comprises a multi-channel image. The multi-channel image can comprise a three-channel image.

In some embodiments, analyzing the plurality of images generated comprises: analyzing the plurality of images generated to determine, for each of the plurality of single cells, the combination of optical detection probe binding sites expressed in the single cell and corresponding predetermined spatial regions using at least one machine learning model, thereby determining the perturbation in the single cell. In some embodiments, the machine learning model comprises a convolutional neural network (CNN). In some embodiments, the machine learning model has a precision of at least 90%, and/or the machine learning model has a recall of at least 90%. In some embodiments, the method comprises: training the machine learning model.

In some embodiments, the plurality of images comprises a plurality of single-channel images, and analyzing the plurality of images using the machine learning model comprises: processing the plurality of single-channel images using the machine learning model. In some embodiments, the plurality of images comprises a plurality of multi-channel images, and analyzing the plurality of images using the machine learning model comprises: processing the plurality of multi-channel images using the machine learning model. In some embodiments, the plurality of images comprises a plurality of multi-channel images, each of the plurality of multi-channel images comprises a plurality of single-channel images, and analyzing the plurality of images using the machine learning model comprises: processing each of the plurality of single-channel images using the machine learning model. In some embodiments, the plurality of images comprises a plurality of multi-channel images, each of the plurality of multi-channel images comprises a plurality of single-channel images, and analyzing the plurality of images using the machine learning model comprises: processing each of the plurality of single-channel images using a corresponding machine learning model.

In some embodiments, analyzing the plurality of images comprises: segmenting the plurality of images to generate a plurality of segmented images each comprising an image of a single cell of the plurality of single cells; and analyzing the plurality of segmented images generated to determine, for each of the plurality of single cells, the combination of optical detection probe binding sites expressed in the single cell and corresponding predetermined spatial regions, thereby determining the perturbation in the single cell.

Disclosed herein include methods for integrated measurements. In some embodiments, a method for integrated measurements comprises: performing integrated measurements using any method for determining (or tracking) perturbations in a plurality of single cells disclosed herein.

Disclosed herein include methods for determining (or tracking) perturbations in a plurality of single cells. In some embodiments, a high-throughput method for determining perturbations in a plurality of single cells is under control of a hardware processor and comprises: receiving a plurality of images of a plurality of single cells. Prior to the plurality of cells being imaged to generate the plurality of images, (i) a plurality of guide ribonucleic acids (gRNAs) comprising a perturbation gRNA ($\Delta$gRNA) and one or more barcode gRNAs, and (ii) a dead CRISPR associated protein 9 (dCas9), the barcode gRNAs each comprises a barcode region comprising zero, one, or more optical detection probe binding sites for a plurality of optical detection probes is expressed in each of the plurality of single cells. The $\Delta$gRNA can bind to a first dCas9 and the first dCas9 bound to the $\Delta$gRNA binds to a chromosome sequence of a genome of the single cell, resulting in a perturbation in the single cell. The barcode gRNAs can bind to a second dCas9 and the second dCas9 bound to the barcode gRNA binds a predetermined spatial region of the genome of the single cell. Presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, can indicate the $\Delta$gRNA is expressed in the single cell. Prior to the plurality of cells being imaged to generate the plurality of images, the plurality of single cells is stained using the plurality of optical detection probes. Two optical detection probes of the plurality of optical detection probes can comprise different optical labels and are capable of binding to two optical detection probe binding sites, of the barcode gRNAs expressed in the plurality of single cells, comprising different sequences. Optical detection probes of the plurality of optical barcodes can bind to the optical detection probe binding sites of the barcode gRNAs expressed in the plurality of single cells. The method can comprise: analyzing the plurality of images generated to determine, for each of the plurality of single cells, the combination of optical detection probe binding sites expressed in the single cell and corresponding predetermined spatial regions, thereby determining the perturbation in the single cell.

Disclosed herein include systems for determining perturbations in a plurality of single cells. In some embodiments, a system for determining perturbations in a plurality of single cells comprises: non-transitory memory configured to store executable instructions; and a hardware processor in communication with the non-transitory memory, the hardware processor programmed by the executable instructions to perform: receiving a plurality of images of a plurality of single cells, wherein prior to the plurality of single cells are imaged to generate the plurality of images: (i) a plurality of guide ribonucleic acids (gRNAs) comprising a perturbation gRNA (ΔgRNA) and one or more barcode gRNAs, and (ii) a dead CRISPR associated protein 9 (dCas9), wherein the barcode gRNAs each comprises a barcode region comprising zero, one, or more optical detection probe binding sites for a plurality of optical detection probes is expressed in each of the plurality of single cells, thereby the ΔgRNA binds to a first dCas9 and the first dCas9 bound to the ΔgRNA binds to a chromosome sequence of a genome of the single cell, resulting in a perturbation in the single cell, and thereby each of the barcode gRNAs binds to a second dCas9 and the second dCas9 bound to the barcode gRNA binds a predetermined spatial region of the genome of the single cell, wherein presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, indicates the ΔgRNA is expressed in the single cell, and the plurality of single cells is stained using the plurality of optical detection probes, wherein two optical detection probes of the plurality of optical detection probes comprise different optical labels and are capable of binding to two optical detection probe binding sites, of the barcode gRNAs expressed in the plurality of single cells, comprising different sequences, thereby optical detection probes of the plurality of optical barcodes bind to the optical detection probe binding sites of the barcode gRNAs expressed in the plurality of single cells. The hardware processor can be programmed by the executable instructions to perform: analyzing the plurality of images generated using a machine learning model to determine, for each of the plurality of single cells, the combination of optical detection probe binding sites expressed in the single cell and corresponding predetermined spatial regions, thereby determining the perturbation in the single cell. The hardware processor can be programmed by the executable instructions to perform: training any machine learning model of the present disclosure.

Disclosed herein include embodiments of a composition comprising a plurality of guide ribonucleic acids (gRNAs) or pluralities of gRNAs disclosed herein. The composition can be for determining perturbations or performing integrated measurements in a plurality of single cells. Disclosed herein include embodiments of a composition comprising a plasmid or a plurality of plasmids disclosed herein. The composition can be for determining perturbations or performing integrated measurements in a plurality of single cells.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 4A and 4B1-4B2. Barcoding with guide RNAs (FIG. 4A) and epitopes (FIG. 4B).

FIGS. 8A, 8B1, 8B2, and 8C-8F. CRISPR-Display for spatial barcoding.

Figure 1:
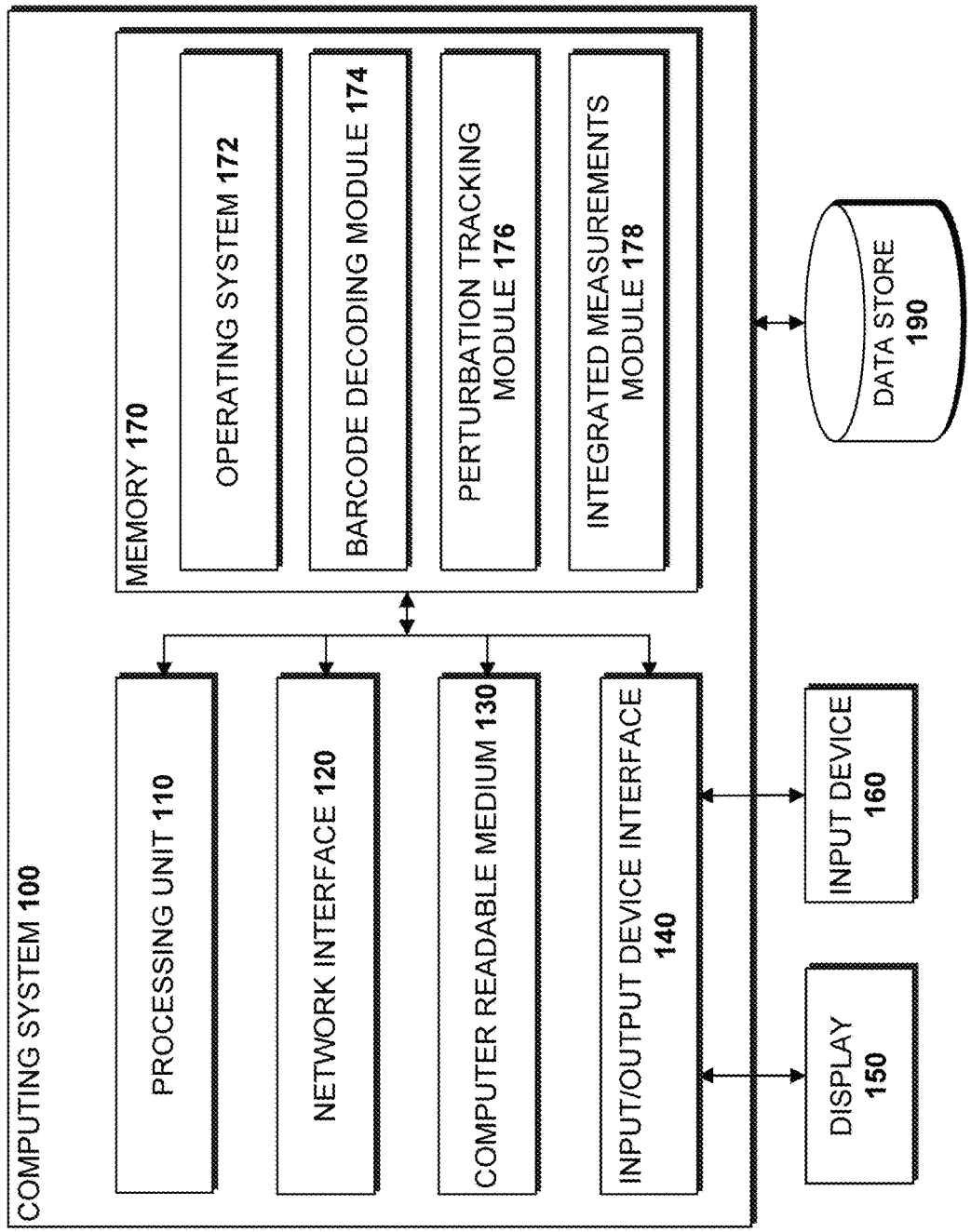
FIG. 1 is a block diagram of an illustrative computing system configured to implement any method disclosed herein, for example, barcode decoding, perturbation tracking, or integrated measurements.

Throughout the drawings, reference numbers may be re-used to indicate correspondence between referenced elements. The drawings are provided to illustrate example embodiments described herein and are not intended to limit the scope of the disclosure.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include high-throughput methods for determining (or tracking) perturbations in a plurality of single cells. In some embodiments, a high-throughput method for determining perturbations in a plurality of single cells comprises expressing in each of a plurality of single cells (i) a plurality of guide ribonucleic acids (gRNAs) comprising a perturbation gRNA (ΔgRNA) and one or more barcode gRNAs (also referred to herein as compartment gRNAs). The barcode gRNAs each can comprise a barcode region comprising zero, one, or more optical detection probe binding sites for a plurality of optical detection probes. The method can comprise expressing in each of the plurality of single cells (ii) a dead CRISPR associated protein 9 (dCas9).

The ΔgRNA can bind to a first dCas9, and the first dCas9 bound to the ΔgRNA can bind to a chromosome sequence of a genome of the single cell, resulting in a perturbation in the single cell. Each of the barcode gRNAs can bind to a second dCas9 and the second dCas9 bound to the barcode gRNA can bind a predetermined spatial region (or compartment or location) of the genome of the single cell. Presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, indicates the ΔgRNA is expressed in the single cell. The method can comprise staining the plurality of single cells with the plurality of optical detection probes. Two optical detection probes of the plurality of optical detection probes can comprise different optical labels and are capable of binding to two optical detection probe binding sites, of the barcode gRNAs expressed in the plurality of single cells, comprising different sequences. Optical detection probes of the plurality of optical barcodes can bind to the optical detection probe binding sites of the barcode gRNAs expressed in the plurality of single cells. The method can comprise imaging the plurality of single cells comprising the optical detection probes bound to the optical detection probe binding sites of the barcode gRNAs expressed in the plurality of single cells to generate a plurality of images. The method can comprise analyzing the plurality of images generated to determine, for each of the plurality of single cells, the combination of optical detection probe binding sites expressed in the single cell and corresponding predetermined spatial regions, thereby determining the perturbation in the single cell.

Disclosed herein include methods for integrated measurements. In some embodiments, a method for integrated measurements comprises: performing integrated measurements using any method for determining (or tracking) perturbations in a plurality of single cells disclosed herein.

Disclosed herein include methods for determining (or tracking) perturbations in a plurality of single cells. In some embodiments, a high-throughput method for determining perturbations in a plurality of single cells is under control of a hardware processor and comprises: receiving a plurality of images of a plurality of single cells. Prior to the plurality of cells being imaged to generate the plurality of images, (i) a plurality of guide ribonucleic acids (gRNAs) comprising a perturbation gRNA (ΔgRNA) and one or more barcode gRNAs, and (ii) a dead CRISPR associated protein 9 (dCas9), the barcode gRNAs each comprises a barcode region comprising zero, one, or more optical detection probe binding sites for a plurality of optical detection probes is expressed in each of the plurality of single cells. The ΔgRNA can bind to a first dCas9 and the first dCas9 bound to the ΔgRNA binds to a chromosome sequence of a genome of the single cell, resulting in a perturbation in the single cell. The barcode gRNAs can bind to a second dCas9 and the second dCas9 bound to the barcode gRNA binds a predetermined spatial region of the genome of the single cell. Presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, can indicate the ΔgRNA is expressed in the single cell. Prior to the plurality of cells being imaged to generate the plurality of images, the plurality of single cells is stained using the plurality of optical detection probes. Two optical detection probes of the plurality of optical detection probes can comprise different optical labels and are capable of binding to two optical detection probe binding sites, of the barcode gRNAs expressed in the plurality of single cells, comprising different sequences. Optical detection probes of the plurality of optical barcodes can bind to the optical detection probe binding sites of the barcode gRNAs expressed in the plurality of single cells. The method can comprise: analyzing the plurality of images generated to determine, for each of the plurality of single cells, the combination of optical detection probe binding sites expressed in the single cell and corresponding predetermined spatial regions, thereby determining the perturbation in the single cell.

Disclosed herein include systems for determining perturbations in a plurality of single cells. In some embodiments, a system for determining perturbations in a plurality of single cells comprises: non-transitory memory configured to store executable instructions; and a hardware processor in communication with the non-transitory memory, the hardware processor programmed by the executable instructions to perform: receiving a plurality of images of a plurality of single cells, wherein prior to the plurality of single cells are imaged to generate the plurality of images: (i) a plurality of guide ribonucleic acids (gRNAs) comprising a perturbation gRNA (ΔgRNA) and one or more barcode gRNAs, and (ii) a dead CRISPR associated protein 9 (dCas9), wherein the barcode gRNAs each comprises a barcode region comprising zero, one, or more optical detection probe binding sites for a plurality of optical detection probes is expressed in each of the plurality of single cells, thereby the ΔgRNA binds to a first dCas9 and the first dCas9 bound to the ΔgRNA binds to a chromosome sequence of a genome of the single cell, resulting in a perturbation in the single cell, and thereby each of the barcode gRNAs binds to a second dCas9 and the second dCas9 bound to the barcode gRNA binds a predetermined spatial region of the genome of the single cell, wherein presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, indicates the ΔgRNA is expressed in the single cell, and the plurality of single cells is stained using the plurality of optical detection probes, wherein two optical detection probes of the plurality of optical detection probes comprise different optical labels and are capable of binding to two optical detection probe binding sites, of the barcode gRNAs expressed in the plurality of single cells, comprising different sequences, thereby optical detection probes of the plurality of optical barcodes bind to the optical detection probe binding sites of the barcode gRNAs expressed in the plurality of single cells. The hardware processor can be programmed by the executable instructions to perform: analyzing the plurality of images generated using a machine learning model to determine, for each of the plurality of single cells, the combination of optical detection probe binding sites expressed in the single cell and corresponding predetermined spatial regions, thereby determining the perturbation in the single cell. The hardware processor can be programmed by the executable instructions to perform: training any machine learning model of the present disclosure.

Disclosed herein include embodiments of a composition comprising a plurality of guide ribonucleic acids (gRNAs) or pluralities of gRNAs disclosed herein. The composition can be for determining perturbations or performing integrated measurements in a plurality of single cells. Disclosed herein include embodiments of a composition comprising a plasmid or a plurality of plasmids disclosed herein. The composition can be for determining perturbations or performing integrated measurements in a plurality of single cells.

Determining Perturbations in Single Cells

Figure 2:
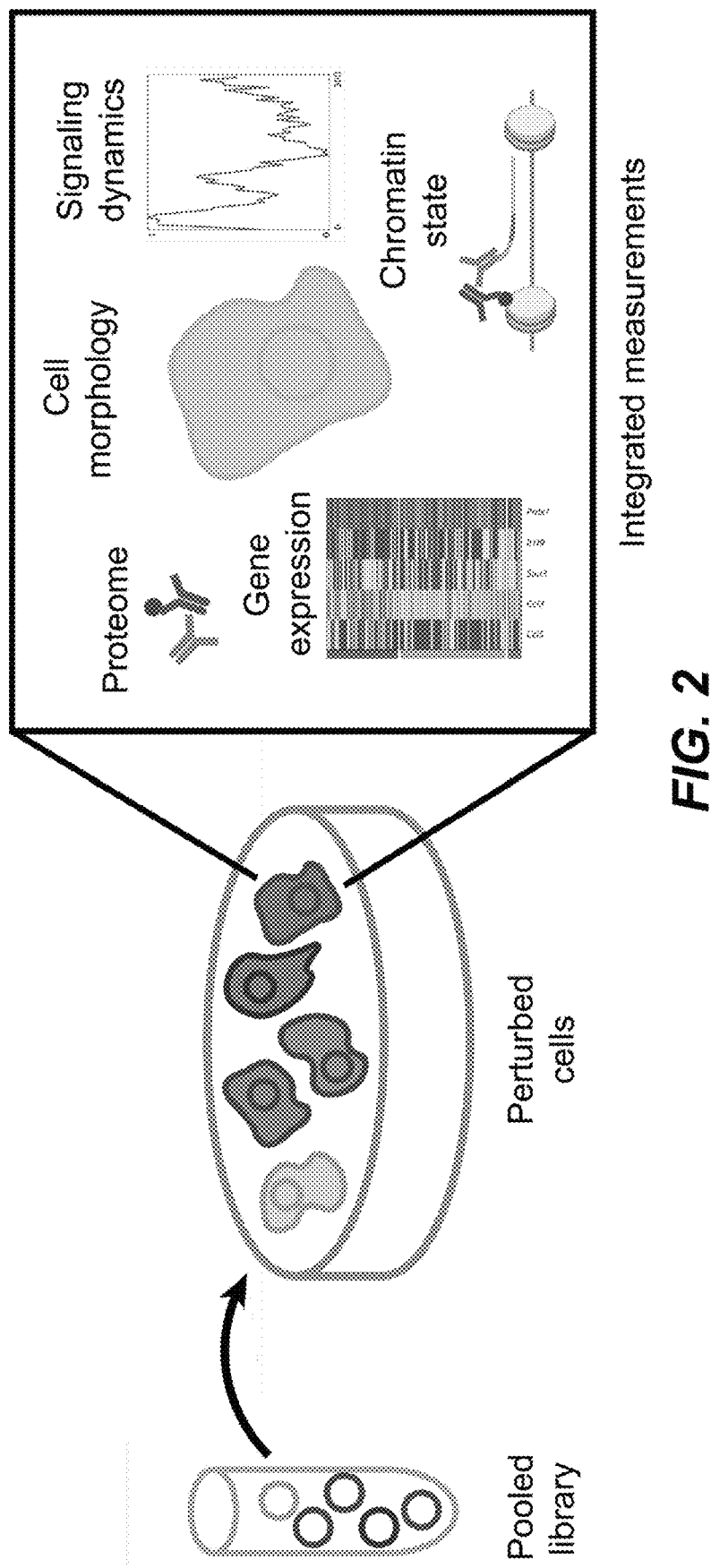
FIG. 2. Example use of a pooled library screen.
Figure 3:
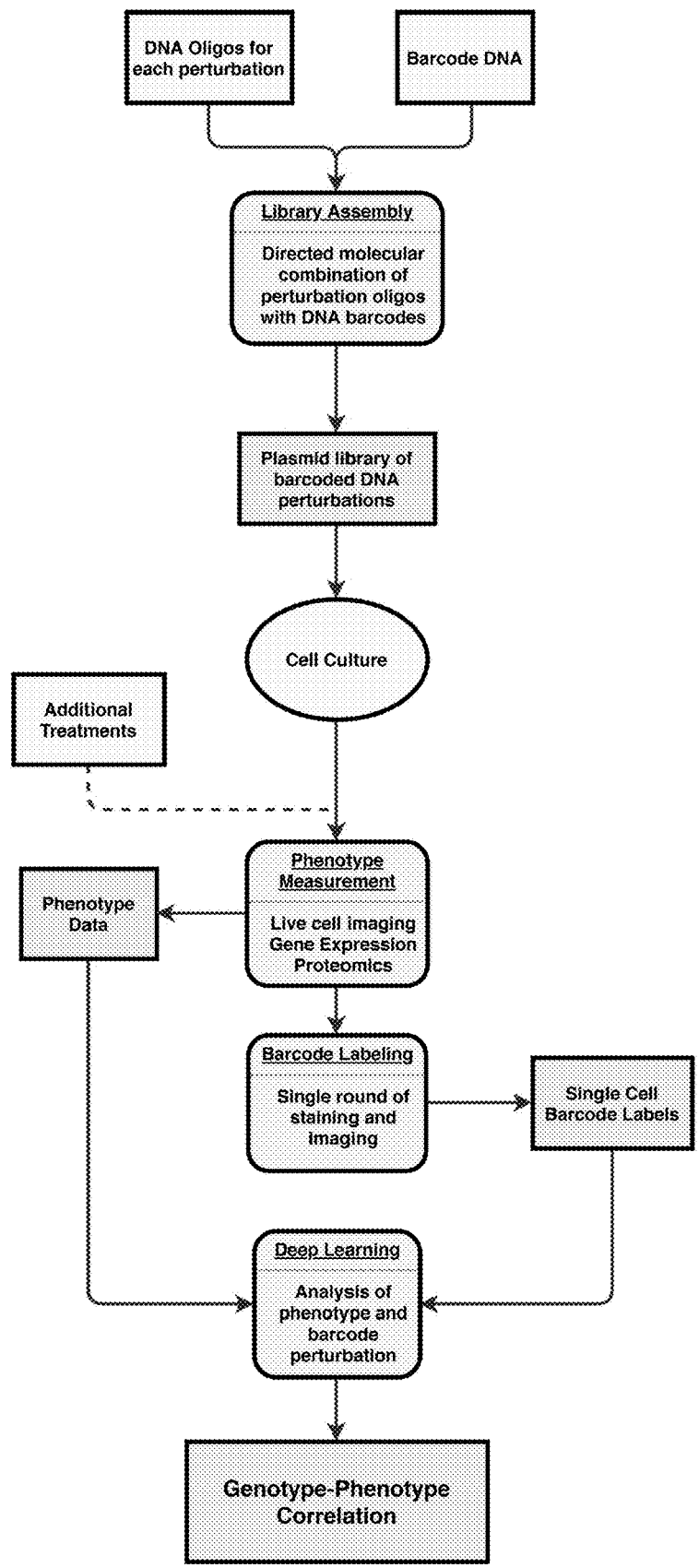
FIG. 3. Example workflow of deep learning enabled spatial optical barcoding for pooled library screens.
Figure 6:
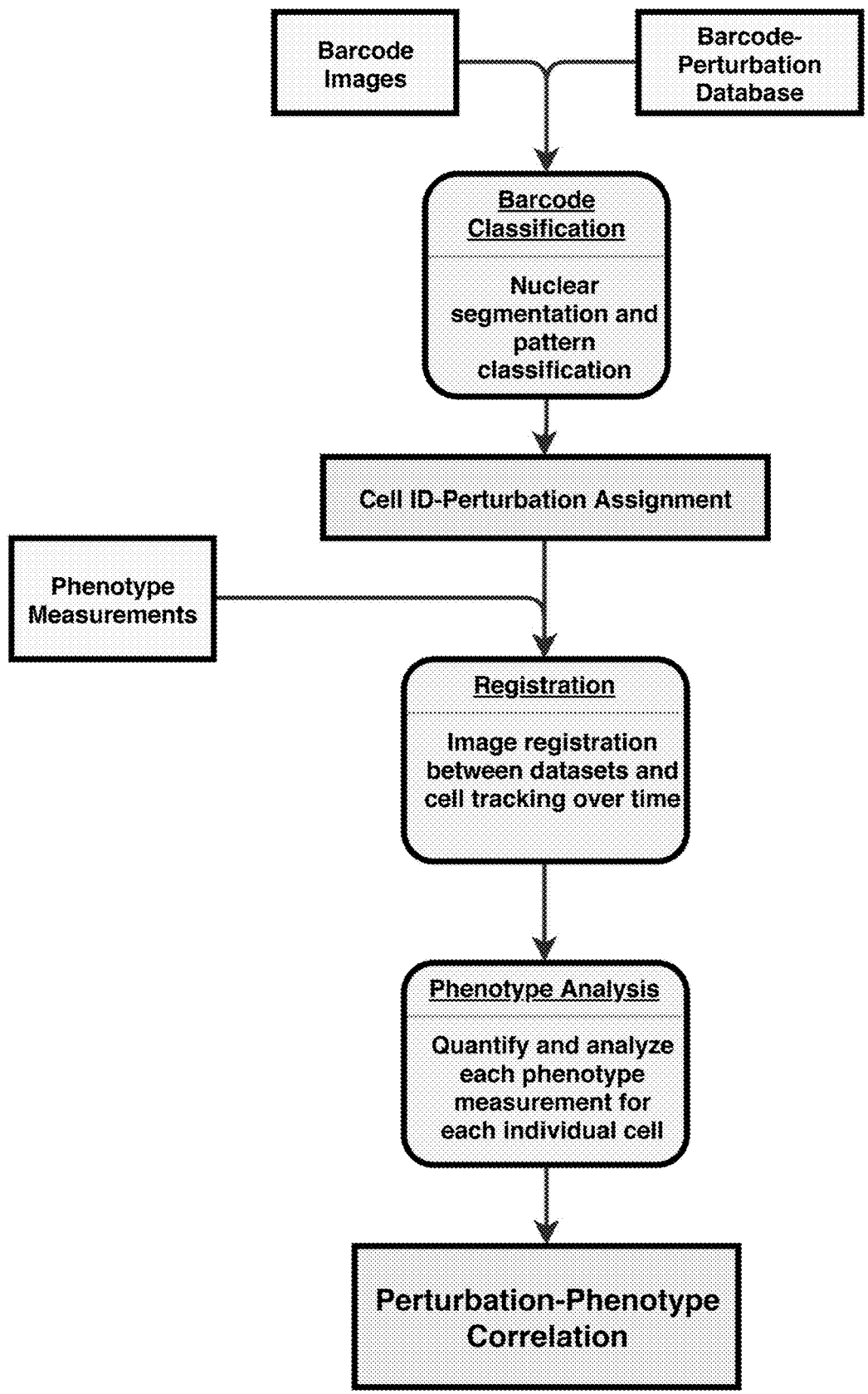
FIG. 6. Example deep learning workflow of spatial optical barcoding for pooled library screens.

Disclosed herein include methods (e.g., high-throughput methods) for determining or tracking perturbations in a plurality of single cells (FIGS. 3 and 6). In some embodiments, a method for determining or tracking perturbations in a plurality of single cells comprises expressing in each of a plurality of single cells (i) a plurality of guide ribonucleic acids (gRNAs) comprising a perturbation gRNA (ΔgRNA) and one or more barcode gRNAs (also referred to herein as compartment gRNAs). The barcode gRNAs each can comprise a barcode region comprising zero, one, or more optical detection probe binding sites for a plurality of optical detection probes (FIGS. 8B1-8B2).

Each of the plurality of single cells can express (ii) a dead CRISPR associated protein 9 (dCas9). The method can comprise expressing in each of the plurality of single cells (ii) a dCas9. The ΔgRNA can bind to a first dCas9, and the first dCas9 bound to the ΔgRNA can bind to a chromosome sequence of a genome of the single cell, resulting in a perturbation in the single cell (FIG. 8F right panel). Each of the barcode gRNAs can bind to a second dCas9 and the second dCas9 bound to the barcode gRNA can bind a predetermined spatial region (or compartment or location) of the genome of the single cell (FIG. 8C). Presence of a combination, of (i) each of the optical detection probe binding sites in the barcode regions of the barcode gRNAs expressed in the single cell and (ii) the corresponding predetermined spatial region (or compartment or location) where the second dCas9 bound to the barcode gRNA comprising the barcode region binds to (FIG. 9), indicates the ΔgRNA is expressed in the single cell (FIG. 8A).

Figure 4A:
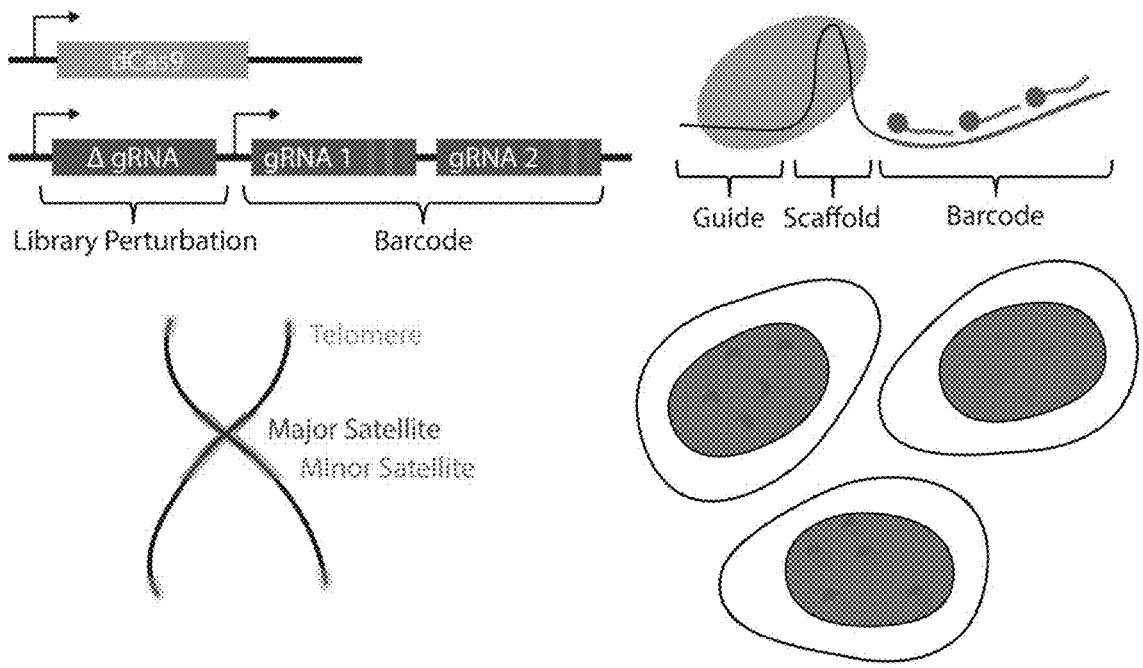
Figure 4A:
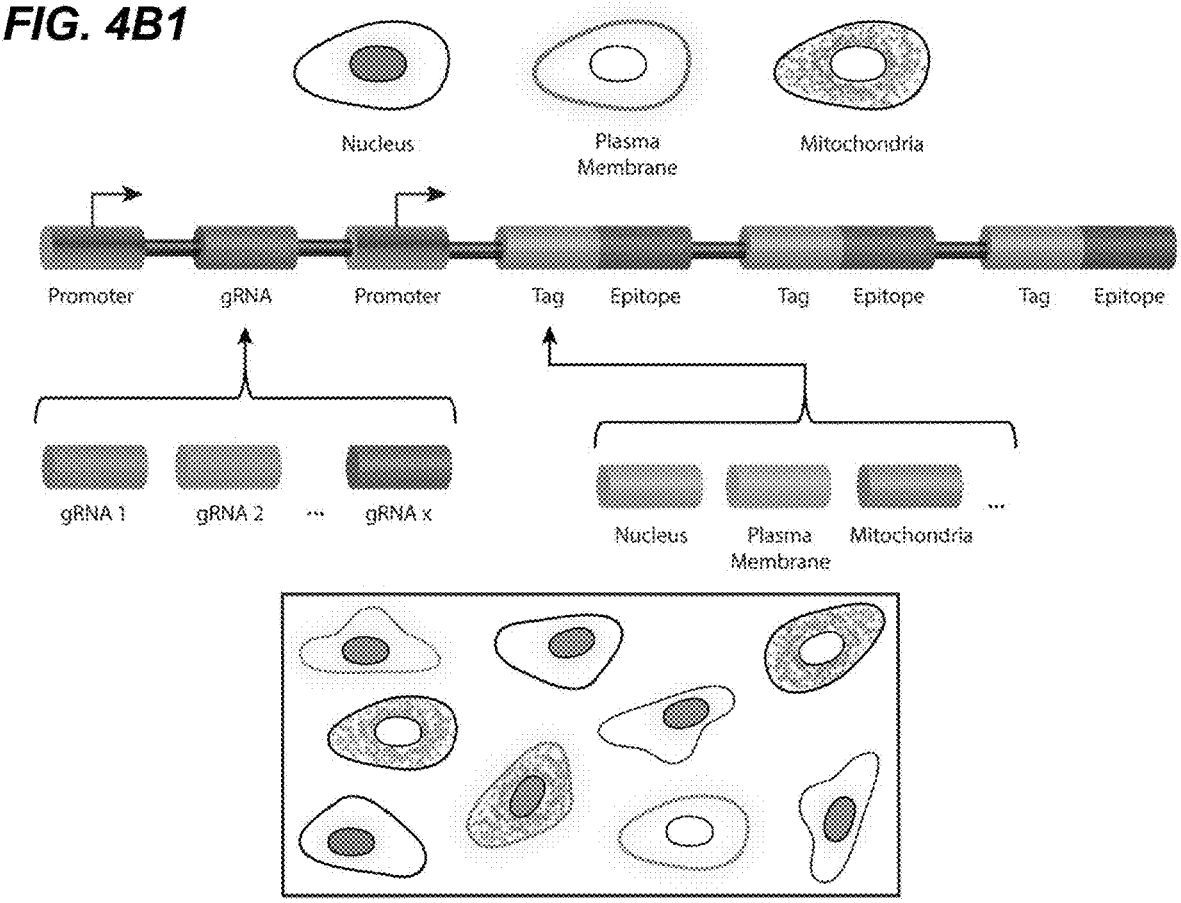
Figure 11A:
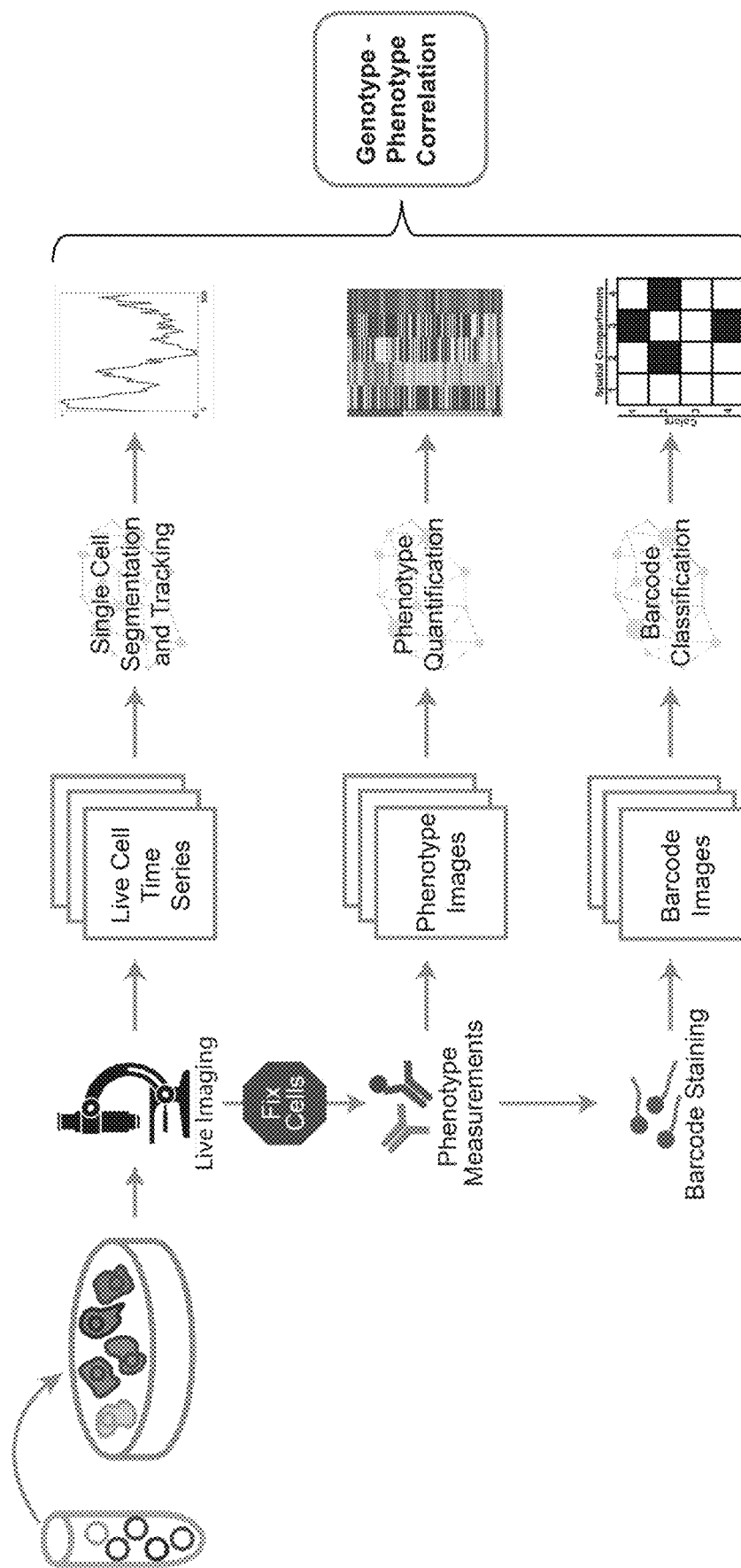
FIGS. 11A-11B. Experimental workflows for an integrated measurement experiment.
Figure 11B:
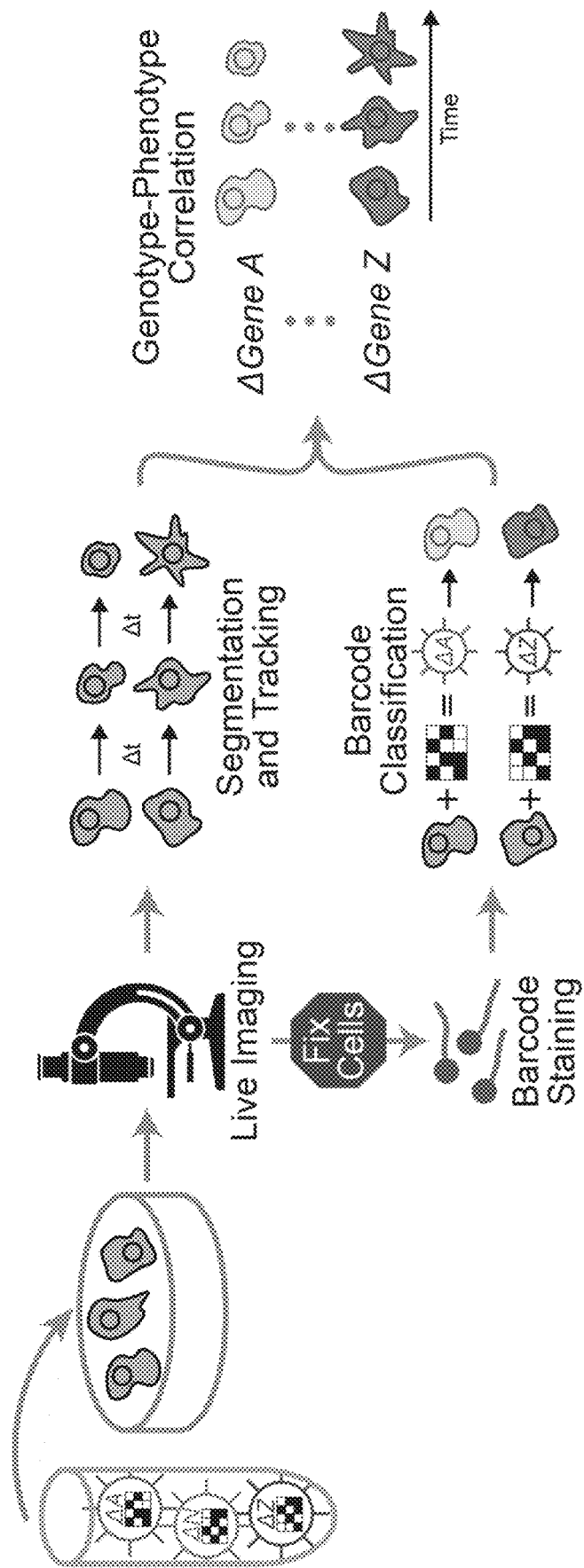

The method can comprise staining the plurality of single cells with the plurality of optical detection probes (FIG. 4A bottom right and 8B1-8B2). Optical detection probes of the plurality of optical barcodes can bind to the optical detection probe binding sites of the barcode gRNAs expressed in the plurality of single cells (FIGS. 8B1-8B2). The method can comprise imaging the plurality of single cells comprising the optical detection probes bound to the optical detection probe binding sites of the barcode gRNAs expressed in the plurality of single cells to generate a plurality of images (e.g., barcode images). The method can comprise analyzing the plurality of images generated to determine, for each of the plurality of single cells, the combination of optical detection probe binding sites expressed in the single cell and corresponding predetermined spatial regions, thereby determining the perturbation in the single cell (FIGS. 11A-11B).

gRNA

In some embodiments, each of the plurality of gRNAs comprises from 5' to 3' a guide region and a scaffold region. The length of a gRNA can be different in different embodiments. In some embodiments, a gRNA is, is about, is at least, is at least about, is at most, or is at most about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, or a number or a range between any two of these values, nucleotides in length. The length of a region of a gRNA (e.g., a guide region, a scaffold region, or a barcode region) can be different in different embodiments. In some embodiments, a region of a gRNA is, is about, is at least, is at least about, is at most, or is at most about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length.

ΔRNA

In some embodiments, each of the plurality of gRNAs comprises from 5' to 3' a guide region and a scaffold region. In some embodiments, each of the plurality of A, gRNAs comprises from 5' to 3' a guide region and a scaffold region (FIG. 8F left panel). Each of the plurality of gRNAs can comprise different numbers of ΔgRNAs. In some embodiments, each of the plurality of gRNAs comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, or a number or a range between any two of these values, ΔgRNAs. For example, each of the plurality of gRNAs comprises at least two ΔgRNAs. Each of the ΔgRNAs can bind to a first dCas9. Each first dCas9 bound to a ΔgRNA binds to a chromosome sequence of the genome of the single cell, resulting in a perturbation in the single cell. Each of the two or more first dCas9s bound to ΔgRNAs bind to a chromosome sequence of the genome of the single cell, collectively resulting in a perturbation in the single cell.

A perturbation can result from the first dCas9 bound to a ΔgRNA binding to a chromosome sequence of the genome of the single cell. A perturbation resulting from the first dCas9s bound to ΔgRNAs binding to chromosome sequences of the genome of the single cell. In some embodiments, a perturbation is repression or activation of transcription. In some embodiments, the perturbation is repression or activation of replication.

In some embodiments, the chromosome sequence of the genome of the single cell the first dCas9 bound to the ΔgRNA binds to is predetermined by a guide region of the ΔgRNA (FIG. 8F). The chromosome sequence of the genome of the single cell the first dCas9 bound to the ΔgRNA binds to can be a reverse complement of a sequence of the guide region of the ΔgRNA (FIG. 8F). In some embodiments, the chromosome sequence of the genome of the single cell comprises a gene of interest, or a subsequence thereof. In some embodiments, the chromosome sequence of the genome of the single cell comprises a promoter of a gene of interest, or a subsequence thereof.

Barcode gRNAs

In some embodiments, each of the plurality of barcode gRNAs comprises from 5' to 3' a guide region and a scaffold region (FIGS. 8B1-8B2). The barcode region can be on 3' end of the gRNA (FIGS. 8B1-8B2). The barcode region can be on 5' end of the gRNA. The scaffold region can comprise the barcode region.

The plurality of gRNAs comprises, comprises about, comprises at least, comprises at least about, comprises at most, or comprises at most about, 1, 2, 3, 4, 5, 6, 7, 8, 9, 10, 11, 12, 13, 14, 15, 16, 17, 18, 19, 20, or a number or a range between any two of these values, barcode gRNAs. For example, the plurality of gRNAs comprises at least three barcode gRNAs. For example, the plurality of gRNAs comprises four barcode gRNAs. Each barcode gRNA can correspond to a spatial region (or compartment or location).

The number of barcode gRNAs expressed in a single cell can be the number of spatial regions (or compartments or locations). The number of spatial regions can be, be about, be at least, be at least about, be at most, or be at most about, 1, 2, 3, 4, 5, 6, 7, 8, 9, 10, 11, 12, 13, 14, 15, 16, 17, 18, 19, 20, or a number or a range between any two of these values.

In some embodiments, the predetermined spatial region (or compartment or location) of the genome of the single cell comprises a repetitive region of the genome of the single cell. The predetermined spatial region of the genome of the single cell can comprise a repetitive region of each chromosome of the genome of the single cell. The predetermined spatial region of the genome of the single cell can comprise a telomere, an alpha satellite, a beta satellite of each chromosome of the genome of the single cell. In some embodiments, the predetermined spatial region of the genome of the single cell that the second dCas9 bound to the barcode gRNA binds to is predetermined by a guide region of the barcode gRNA. The predetermined spatial region of the genome of the single cell and/or the guide region of the barcode gRNA can comprise a sequence of 5'-GAATCTGCAAGTGGATATT-3' (SEQ ID NO: 1), 5'-AGGTGATGTAACTCTTGTCT-3' (SEQ ID NO: 2), 5'-GTTAGGGTTAGGGTTAGGGTTA-3' (SEQ ID NO: 3), a reverse complement of any of the proceeding, or a combination thereof.

The number (or maximum number) of optical detection probe binding sites in a barcode region of a barcode gRNA can be different in different embodiments. In some embodiments, the number (or maximum number) of optical detection probe binding sites in a barcode region of a barcode gRNA is, is about, is at least, is at least about, is at most, or is at most about, 0, 1, 2, 3, 4, 5, 6, 7, 8, 9, 10, 11, 12, 13, 14, 15, 16, 17, 18, 19, 20, or a number or a range between any two of these values. For example, the barcode region of a barcode gRNA comprises at least three optical detection probe binding sites. The number (or maximum number) of optical detection probe binding sites can be the number of optical labels (or the number of colors) of the plurality of optical detection probes.

The length of an optical detection probe binding site can be different in different embodiments. In some embodiments, an optical detection probe binding site is, is about, is at least, is at least about, is at most, or is at most about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length.

Barcodes

In some embodiments, the barcode region of a barcode gRNA comprises presence or absence of each of the possible optical detection probe binding sites (e.g., each of at least three possible optical detection probe binding sites). For example, a first barcode gRNA can comprise a binding site for a blue optical detection probe, a binding site for a green optical detection probe, and a binding site for a red optical detection probe (FIGS. 8B1-8B2), and a second brocade gRNA can comprise the binding site for the blue optical detection probe and the binding site for the green optical detection probe and not the binding site for the red optical detection probe. The length of the first barcode gRNA and the second barcode gRNA can be different because the second barcode gRNA lacks the binding site for the red optical detection probe. The second barcode gRNA can comprise a sequence in the place of the binding site for the red optical detection probe such that the length of the first barcode gRNA and the second barcode gRNA are the same or similar.

In some embodiments, a combination of an optical detection probe binding site expressed in each of the plurality of single cells and the corresponding predetermined spatial region represents a barcode subunit (or spatial optical barcode subunit). The combination of optical detection probe binding sites expressed in each of the plurality of single cells and the corresponding predetermined spatial regions can represent a barcode (or spatial optical barcode) comprising a plurality of barcode subunits (or spatial optical barcode subunits).

Figure 9:
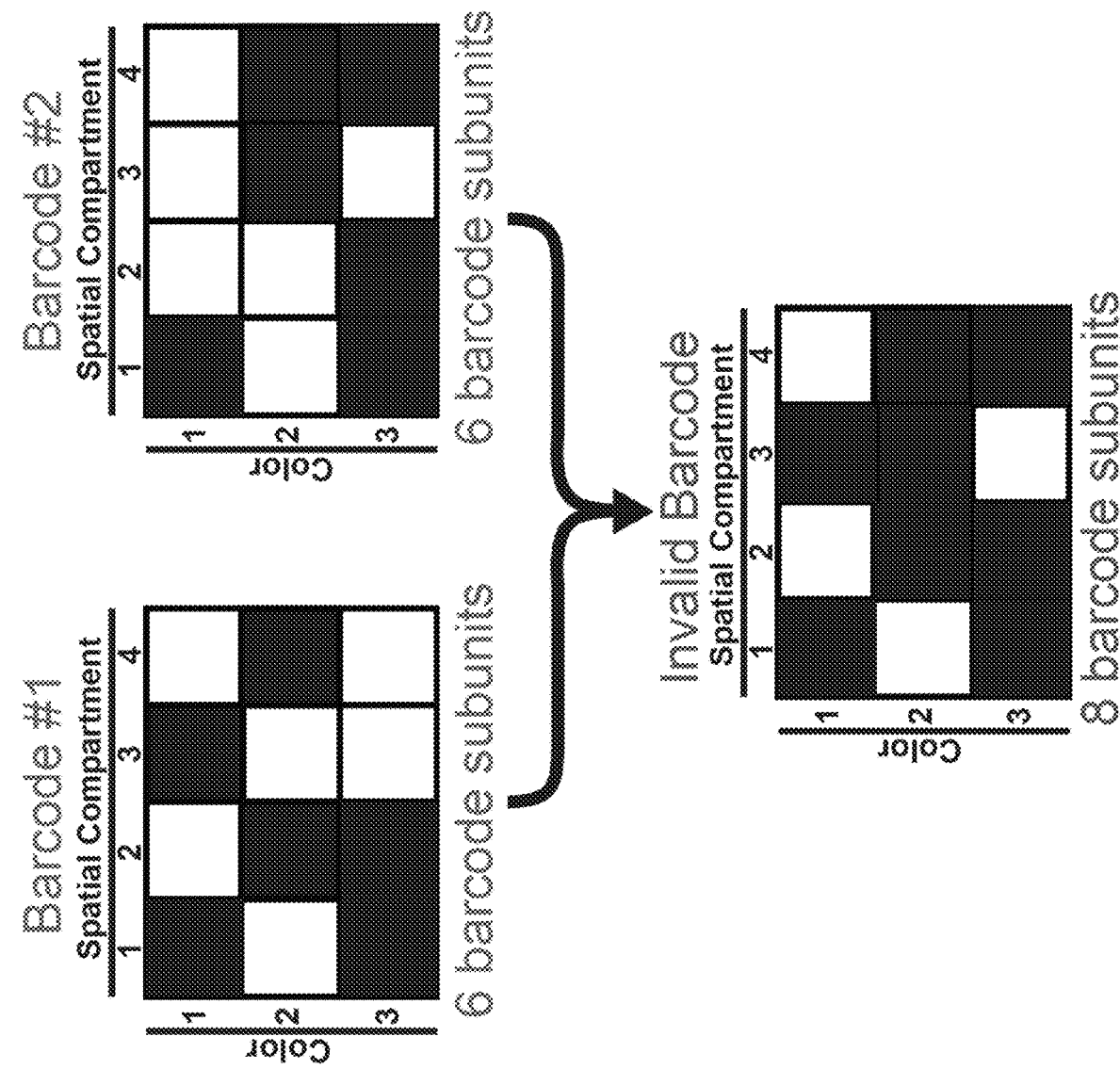
FIG. 9. An error detection scheme for identifying multiple infections.

In some embodiments, a combination of an optical label of an optical detection probe bound to a barcode gRNA expressed in each of the plurality of single cells and the corresponding predetermined spatial region represents a barcode subunit (FIG. 9). The combination of optical labels of optical detection probes bound to barcode gRNAs expressed in each of the plurality of single cells and the corresponding predetermined spatial regions can represent a barcode (or spatial optical barcode) comprising a plurality of barcode subunits (or spatial optical barcode subunits). Each of the plurality of barcode subunits can be selected from a plurality of possible barcode subunits In some embodiments, a number of the plurality of possible barcode subunits is (number of the optical detection probe binding sites of the barcode region in each of the barcode gRNAs)×(number of the barcode gRNAs) or (maximum number of the optical detection probe binding sites of the barcode region in each of the barcode gRNAs)×(number of the barcode gRNAs).

In some embodiments, a number of the plurality of possible barcode subunits is (number of different optical labels of the plurality of optical detection probes)×(number of the predetermined spatial regions).

The number of the plurality of possible barcode subunits can be different in different embodiments. In some embodiments, the number of possible subunits is, is about, is at least, is at least about, is at most, or is at most about, 4, 5, 6, 7, 8, 9, 10, 11, 12, 13, 14, 15, 16, 17, 18, 19, 20, 21, 22, 23, 24, 25, 26, 27, 28, 29, 30, or a number or a range between any two of these values. For example, the number of the plurality of possible barcode subunits is about 12 (also referred to herein as a 12-subunit barcode). In some embodiments, the barcode comprises six of the plurality of possible barcode subunits (also referred to herein as a six-subunit barcode).

The barcode can comprise fewer than all of the plurality of possible barcode subunits (FIG. 9). In some embodiments, the barcode comprises, comprises about, comprises at least, comprises at least about, comprises at most, or comprises at most about, 10%, 20%, 30%, 40%, 50%, 60%, 70%, 80%, 90%, or a number or a range between any two of these values, of the plurality of possible barcode subunits. For example, the barcode comprises about half of the plurality of possible barcode subunits.

In some embodiments, presence of any of the remaining of the plurality of possible barcode subunits in the barcode indicates an error has occurred. In some embodiments, the method comprises performing error detection using the remaining of the plurality of possible barcode subunits. In some embodiments, the number of possible barcodes is $$\frac{(n \times m)!}{\left(\frac{n \times m}{2}\right)! \left(\frac{n \times m}{2}\right)!},$$

where n denotes a number of the optical detection probe binding sites of the barcode region in each of the barcode gRNAs and m denotes a number of the barcode gRNAs, or n denotes a number of different optical labels of the plurality of optical detection probes and m denotes a number of the predetermined spatial regions (or compartments or locations).

The number of barcodes can be the same as the number of possible barcodes. The number of barcodes can be smaller than the number of possible barcodes because, for example, a barcode comprises fewer than all of the possible barcode subunits. The number of barcodes can be different in different embodiments. In some embodiments, the number of possible barcodes is, is about, is at least, is at least about, is at most, or is at most about, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, $10^5$, $10^6$, $10^7$, $10^8$, $10^9$, $10^{10}$, or a number or a range between any two of these values. For example, the number of barcodes is about 1000.

In some embodiments, a number of possible barcodes is $2^{(the\ number\ of\ the\ plurality\ of\ barcode\ subunits)} - 1$. The number of possible barcodes (or the size of the coding space) can be different in different embodiments. In some embodiments, the number of possible barcodes is, is about, is at least, is at least about, is at most, or is at most about, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, $10^5$, $10^6$, $10^7$, $10^8$, $10^9$, $10^{10}$, or a number or a range between any two of these values. For example, the number of possible barcodes can be at least 4000.

Perturbations

The number of perturbations can be the number of barcodes. The number of perturbations can be different in different embodiments. In some embodiments, the number of perturbations is, is about, is at least, is at least about, is at most, or is at most about, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, $10^5$, $10^6$, $10^7$, $10^8$, $10^9$, $10^{10}$, or a number or a range between any two of these values. For example, a number of the perturbations is about 1000. For example, a number of the perturbations is at least 4000.

Plasmid

In some embodiments, expressing in each of the plurality of single cells the plurality of gRNAs comprises: introducing a plasmid comprising a plurality of gRNAs (FIG. 10E) into each of the plurality of single cells. In some embodiments, the plasmid is a viral vector. The plasmid can be a lentiviral vector. In some embodiments, introducing a plasmid comprising a plurality of gRNAs into each of the plurality of single cells comprises: introducing a plasmid comprising a plurality of gRNAs into each of the plurality of single cells comprises at a multiplicity of infection (MOI) of about 0.5. The MOI can be different in different embodiments. In some embodiments, the MOI is, is about, is at least, is at least about, or is at most about, 0.1, 0.2, 0.3, 0.4, 0.5, 0.6, 0.7, 0.8, 0.9, 1, or a number or a range between any two of these values.

Figure 5:
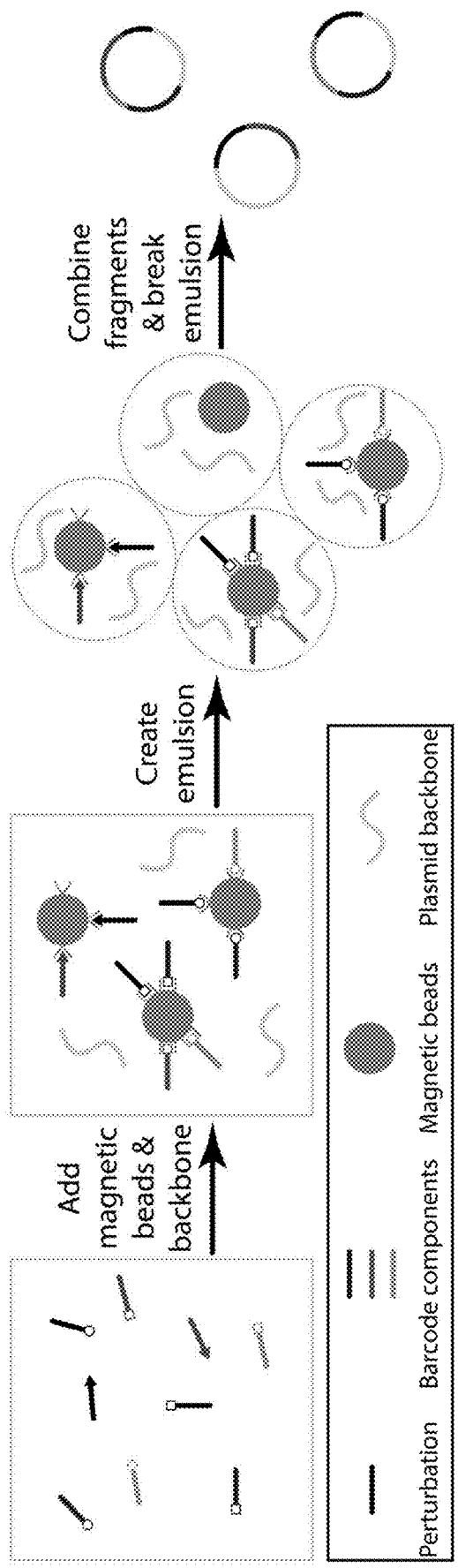
FIG. 5. Combinatorial assembly of library.
Figure 10A:
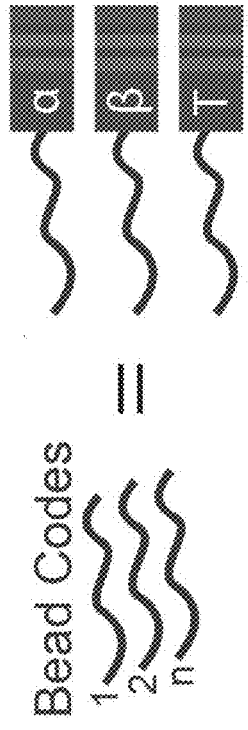
FIGS. 10A-10F. Exemplary components for assembling a library of barcoded plasmids.
Figure 10B:
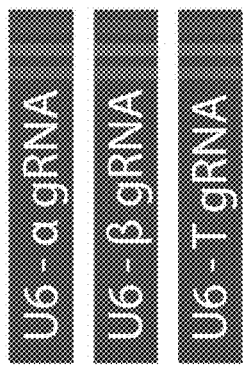
Figure 10C:
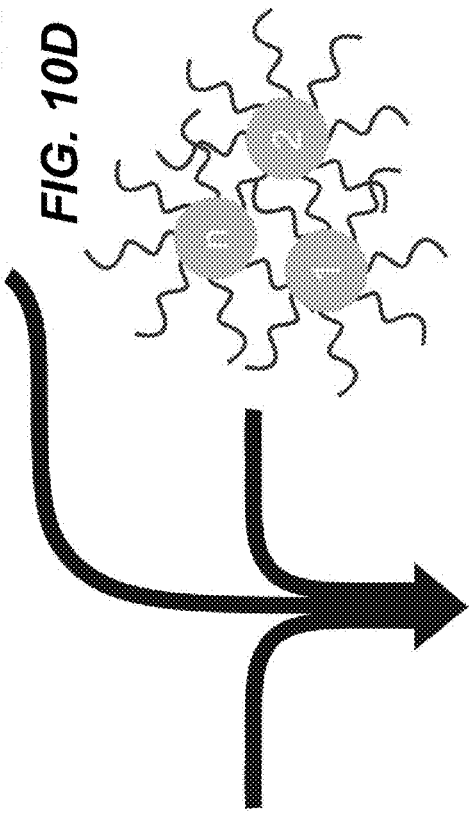
Figure 10D:
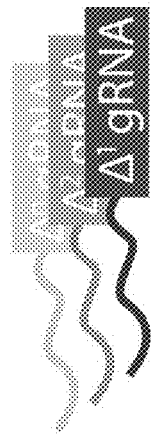
Figure 10E:
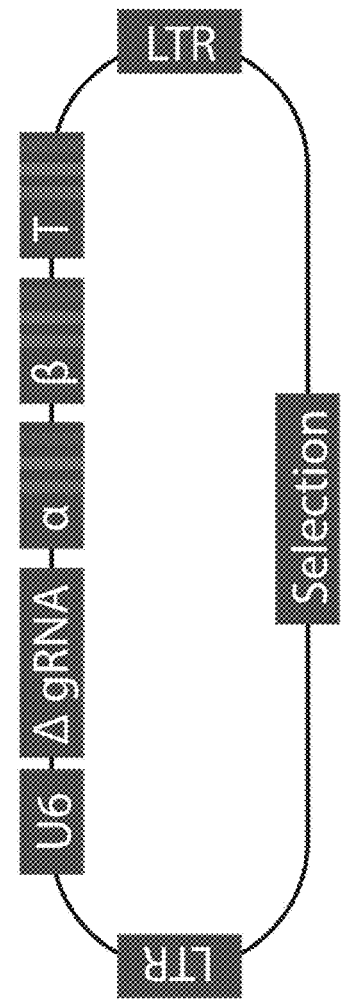

In some embodiments, the method comprises assembling a plasmid comprising the plurality of gRNAs expressed in one of the plurality of single cells (FIGS. 5 and 10A-10E). Assembling the plasmid can comprise: hybridizing the plurality of gRNAs comprising an identical bead code to a bead comprising the bead code, or a reverse complement thereof (FIG. 5) and ligating the plurality of gRNAs to form a plasmid comprising the plurality of gRNAs (FIGS. 5 and 10E).

In some embodiments, the method comprises assembling a plurality of plasmids each comprising the plurality of gRNAs expressed in one of the plurality of single cells. Assembling the plurality of plasmids can comprise for each of the pluralities of gRNAs expressed in one of the plurality of single cells, hybridizing the plurality of gRNAs comprising an identical bead code to a bead of a plurality of beads comprising the bead code, or a reverse complement thereof in a first partition (FIG. 5 middle left panel). gRNAs of each of the pluralities of gRNAs can comprise a different bead code. Assembling the plurality of plasmids can comprise partitioning each of the plurality of beads into one of a plurality of second partitions (FIG. 5 middle right panel) releasing the plurality of gRNAs hybridized to the bead in each of the plurality of second partitions from the bead. Assembling the plurality of plasmids can comprise ligating the plurality of gRNAs in each of the plurality second partitions to form a plasmid comprising the plurality of gRNAs in each second partition (FIG. 5 right panel).

Assembling the plurality of plasmids can comprise for each of the pluralities of gRNAs expressed in one of the plurality of single cells: co-partitioning the barcode gRNAs of the plurality of gRNAs and a unique bead code into a first partition (FIG. 10A); and generating the plurality of barcode gRNAs comprising the bead code in the first partition (FIG. 10B). Assembling the plurality of plasmids can comprise hybridizing each of the pluralities of barcode gRNAs comprising the bead code and a ΔgRNA comprising the bead code to a bead, of a plurality of beads, comprising the bead code, or a reverse complement thereof, in a second partition (FIGS. 10C-10D). Assembling the plurality of plasmids can comprise partitioning each of the plurality of beads into a third partition of a plurality of third partitions. Assembling the plurality of plasmids can comprise releasing the barcode gRNAs and the ΔgRNA hybridized to the bead in each of the plurality of third partitions from the bead. Assembling the plurality of plasmids can comprise ligating the barcode gRNAs and ΔgRNA in each of the plurality of third partitions to form a plasmid comprising the plurality of gRNAs in the third partition. In some embodiments, the method comprises: synthesizing the ΔgRNAs comprising the bead codes (FIG. 10C). In some embodiments, the method comprises releasing the plurality of plasmids. In some embodiments, the method comprises purifying the plurality of plasmids. In some embodiments, the method comprises amplifying the plurality of plasmids.

Single Cells

The number of the plurality of single cells can be different in different embodiments. In some embodiments, the number of the plurality of single cells is, is about, is at least, is at least about, is at most, or is at most about, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, $10^5$, $10^6$, $10^7$, $10^8$, $10^9$, $10^{10}$, or a number or a range between any two of these values. For example, a number of the plurality of single cells is about 1000. For example, a number of the plurality of single cells is at least 4000.

A number of single cells can express an identical gRNA (or identical gRNAs). In some embodiments, the number of single cells expressing an identical gRNA (or identical gRNAs) is, is about, is at least, is at least about, is at most, or is at most about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 1600, 170, 180, 190, 200, 300, 400, 500, 600, 700, 800, 900, 1000, or a number or a range between any two of these values. For example, an identical gRNA is expressed in two or more single cells of the plurality of single cells. In some embodiments, every single cell expresses a different gRNA (or different gRNAs).

An identical plasmid is introduced into a number of single cells. In some embodiments, the number of single cells comprising an identical plasmid is, is about, is at least, is at least about, is at most, or is at most about, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 1600, 170, 180, 190, 200, 300, 400, 500, 600, 700, 800, 900, 1000, or a number or a range between any two of these values. For example, an identical plasmid is introduced into two or more single cells of the plurality of single cells, such as 150 single cells.

In some embodiments, the perturbations in the single cells expressing an identical gRNA (or identical gRNAs) or containing an identical plasmid are different. In some embodiments, the perturbations in the single cells expressing an identical gRNA (or identical gRNAs) or containing an identical plasmid are the same.

Expressing

Figure 10F:
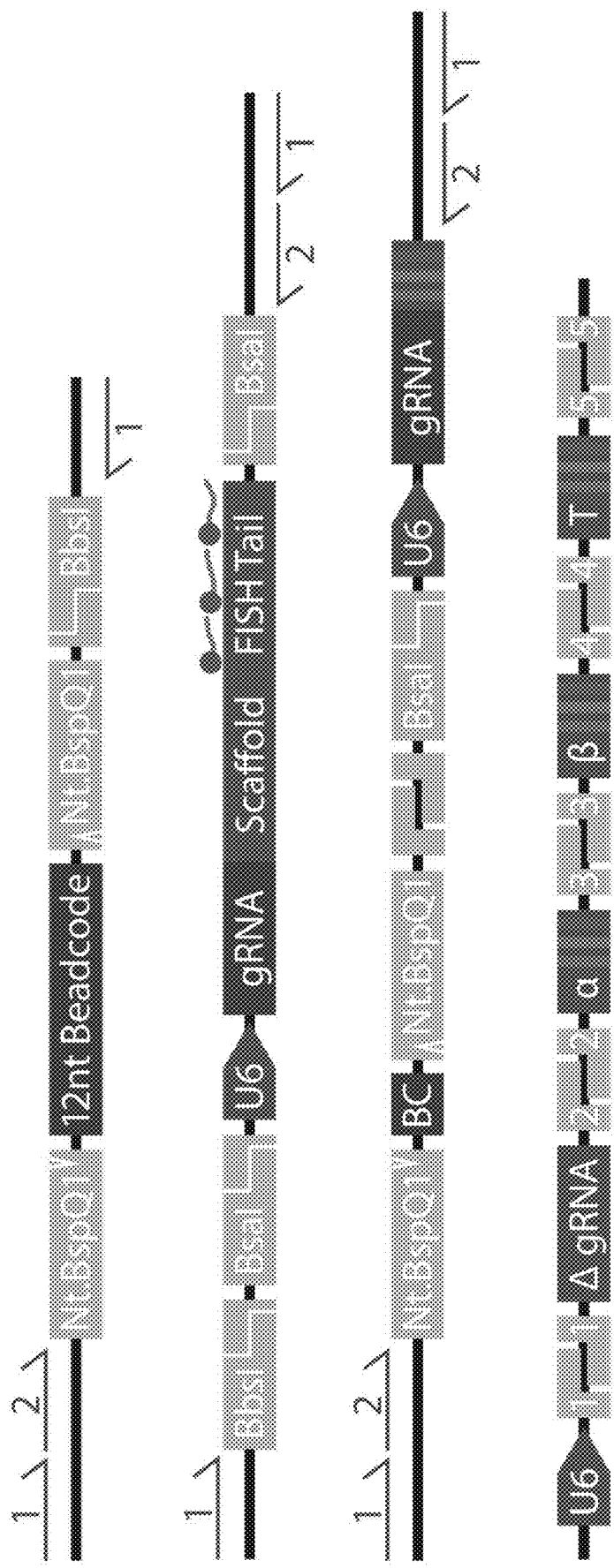

In some embodiments, the plurality of gRNAs is under transcription control of a promoter (FIG. 10E). Two or more of the plurality of gRNAs can be under control of a promoter (FIG. 10F). Each of the plurality of gRNAs can under control of a promoter (FIG. 10F). In some embodiments, the promoter is a U6 promoter. In some embodiments, the method comprises culturing the plurality of single cells.

Optical Detection Probes

Two optical detection probes with different optical labels can comprise an identical sequence or are capable of binding to the same optical detection label probe site. Two optical detection probes with different optical labels can comprise different sequences or are capable of binding to different optical detection probe binding sites. Two optical detection probes with an identical optical label can comprise different sequences or are capable of binding to different optical detection probe binding sites.

In some embodiments, two or more optical detection probes of the plurality of optical detection probes comprise different optical labels and are capable of binding to two optical detection probe binding sites, of the barcode gRNAs expressed in the plurality of single cells, comprising different sequences. Each optical detection probe of the plurality of optical detection probes can comprise a different optical label and is capable of binding to a different binding sites, of the barcode gRNAs expressed in the plurality of single cells, comprising a different sequence. In some embodiments, two or more optical detection probes of the plurality of optical detection probes comprise an identical optical label and are capable of binding to two optical detection probe binding sites, of the barcode gRNAs expressed in the plurality of single cells, comprising different sequences.

The number of optical detection probes (with different optical labels, different sequences, and/or are capable of binding to different optical detection probe binding site) can be different in different embodiments. In some embodiments, the number of optical detection probes is, is about, is at least about, is at most, or is at most about, 2, 3, 4, 5, 6, 7, 8, 9, 10, 11, 12, 13, 14, 15, 16, 17, 18, 19, 20, or a number or a range between any two of these values. The number of optical labels can be different in different embodiments. In some embodiments, the number of optical labels is, is about, is at least about, is at most, or is at most about, 2, 3, 4, 5, 6, 7, 8, 9, 10, 11, 12, 13, 14, 15, 16, 17, 18, 19, 20, or a number or a range between any two of these values.

In some embodiments, each of the plurality of optical detection probes comprises one of at least three optical labels. In some embodiments, the plurality of optical detection probes comprises a plurality of fluorescent oligonucleotides. An optical label can be a fluorescent label, and an optical detection probe can be a fluorescent probe. In some embodiments, optical detection probes of the plurality of optical barcodes bind directly to the optical detection probe binding sites of the barcode gRNAs expressed in the plurality of single cells (FIG. 8B1). In some embodiments, optical detection probes of the plurality of optical barcodes bind indirectly to the optical detection probe binding sites of the barcode gRNAs expressed in the plurality of single cells via concatemer probes that bind directly to the optical detection probe binding sites of the barcode gRNAs expressed in the plurality of single cells (FIG. 8B2).

Staining

The plurality of single cells can be imaged at different magnifications to generate the plurality of images in different embodiments. In some embodiments, the plurality of single cells is imaged at 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, 100×, or a number or a range between any two of these values, magnification. For example, the plurality of single cells is imaged at 40× magnification to generate the plurality of images.

The number of round(s) of staining and imaging can be different in different embodiments. In some embodiments, the number of round(s) of staining and imaging is, is about, is at least, is at least, is at most, or is at most about, 1, 2, 3, 4, 5, 6, 7, 8, 9, 10, or a number or a range between any two of these values. For example, staining the plurality of single cells with the plurality of optical detection probes comprises one round of staining. For example, staining the plurality of single cells with the plurality of optical detection probes comprises at most two rounds of staining. One round of staining can be sufficient to differential about 4000 barcodes. One round of staining can be sufficient to differential about 1000 barcodes with error detection.

Imaging

In some embodiments, an image of the plurality of images comprises a single-channel image. In some embodiments, an image of the plurality of images comprises a multi-channel image. The number of channels in a multi-channel image can be, be about, be at least, be at least about, be at most, be at most about, 2, 3, 4, 5, 6, 7, 8, 9, 10, or a number or a range between any two of these values. The multi-channel image can comprise a three-channel image.

The methods and compositions disclosed herein can be used to analyze/process images produced in various types of microscopes, for example microscopes that can image at least one, two, three, four, or more simultaneous color channels. In some embodiments, the images are produced using microscopes that are capable of imaging at most, or at most about, ten, nine, eight, seven, six, five, four, three, or two simultaneous color channels. In some embodiments, the images are produced using microscopes that are capable of imaging ten, nine, eight, seven, six, five, four, three, two, or a range between any two of these values, simultaneous color channels.

Analyzing

In some embodiments, analyzing the plurality of images generated comprises: analyzing the plurality of images generated to determine, for each of the plurality of single cells, the combination of optical detection probe binding sites expressed in the single cell and corresponding predetermined spatial regions using at least one machine learning model, thereby determining the perturbation in the single cell. In some embodiments, the machine learning model comprises a deep learning model (FIG. 3). In some embodiments, the machine learning model comprises a convolutional neural network (CNN). The precision and/or the recall of the machine learning model can be different in different embodiments. In some embodiments, the precision and/or the recall of the machine learning model is, is about, is at least, is at least about, is at most, or is at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, the machine learning model has a precision of at least 90%, and/or the machine learning model has a recall of at least 90%. In some embodiments, the method comprises: training the machine learning model.

In some embodiments, the plurality of images comprises a plurality of single-channel images, and analyzing the plurality of images using the machine learning model comprises: processing the plurality of single-channel images using the machine learning model. In some embodiments, the plurality of images comprises a plurality of multi-channel images, and analyzing the plurality of images using the machine learning model comprises: processing the plurality of multi-channel images using the machine learning model. In some embodiments, the plurality of images comprises a plurality of multi-channel images, each of the plurality of multi-channel images comprises a plurality of single-channel images, and analyzing the plurality of images using the machine learning model comprises: processing each of the plurality of single-channel images using the machine learning model. In some embodiments, the plurality of images comprises a plurality of multi-channel images, each of the plurality of multi-channel images comprises a plurality of single-channel images, and analyzing the plurality of images using the machine learning model comprises: processing each of the plurality of single-channel images using a corresponding machine learning model.

In some embodiments, analyzing the plurality of images comprises: segmenting the plurality of images to generate a plurality of segmented images each comprising an image of a single cell of the plurality of single cells; and analyzing the plurality of segmented images generated to determine, for each of the plurality of single cells, the combination of optical detection probe binding sites expressed in the single cell and corresponding predetermined spatial regions, thereby determining the perturbation in the single cell.

Barcode Decoding

Disclosed herein include methods for determining barcodes (or barcode decoding). In some embodiments, a method for determining barcodes is under control of a hardware processor and comprises: receiving a plurality of images of a plurality of single cells. Prior to the plurality of cells being imaged to generate the plurality of images, (i) a plurality of guide ribonucleic acids (gRNAs) comprising a perturbation gRNA (ΔgRNA) and one or more barcode gRNAs, and (ii) a dead CRISPR associated protein 9 (dCas9), the barcode gRNAs each comprises a barcode region comprising zero, one, or more optical detection probe binding sites for a plurality of optical detection probes is expressed in each of the plurality of single cells. The ΔgRNA can bind to a first dCas9 and the first dCas9 bound to the ΔgRNA binds to a chromosome sequence of a genome of the single cell, resulting in a perturbation in the single cell. The barcode gRNAs can bind to a second dCas9 and the second dCas9 bound to the barcode gRNA binds a predetermined spatial region of the genome of the single cell. Prior to the plurality of cells being imaged to generate the plurality of images, the plurality of single cells is stained using the plurality of optical detection probes. Optical detection probes of the plurality of optical barcodes can bind to the optical detection probe binding sites of the barcode gRNAs expressed in the plurality of single cells.

Presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, can indicate the ΔgRNA is expressed in the single cell. The combination of optical detection probe binding sites expressed in each of the plurality of single cells and the corresponding predetermined spatial regions represents a barcode (or spatial optical barcode). The method can comprise: analyzing the plurality of images generated, for example, using a machine learning model to determine, for each of the plurality of single cells, the combination of optical detection probe binding sites expressed in the single cell and corresponding predetermined spatial regions, thereby determining a barcode associated with each of the single cell. The method can comprise determining a perturbation resulting from the ΔgRNA binding to the chromosome sequence of the genome of the single cell using the barcode determined and the correspondence between the barcode and the ΔgRNA expressed in the single cell (or the expression of the barcode gRNAs encoding the barcode and the ΔgRNA in the single cell).

Integrated Measurements

Disclosed herein include methods for integrated measurements (FIGS. 2, 3, 6, 7, 11A, and 11B). In some embodiments, a method for integrated measurements comprises: performing integrated measurements (e.g., determining genotype-phenotype or perturbation-phenotype correlations) using any method for determining barcodes or determining (or tracking) perturbations in a plurality of single cells disclosed herein.

Compositions

Disclosed herein include embodiments of a composition comprising a plurality of guide ribonucleic acids (gRNAs) or pluralities of gRNAs disclosed herein. The composition can be used for determining perturbations or performing integrated measurements in a plurality of single cells. Disclosed herein include embodiments of a composition comprising a plasmid or a plurality of plasmids disclosed herein. The composition can be used for determining perturbations or performing integrated measurements in a plurality of single cells.

Machine Learning Model

One or more computer vision models can be implemented for barcode decoding, perturbation tracking, or integrated measurements. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth. One or more of these computer vision algorithms can be used for barcode decoding, perturbation tracking, or integrated measurements.

Once trained, a machine learning model can be stored in a computing system (e.g., the computing system 100 described with reference to FIG. 1). Some examples of machine learning models can include supervised or non-supervised machine learning, including regression models (such as, for example, Ordinary Least Squares Regression), instance-based models (such as, for example, Learning Vector Quantization), decision tree models (such as, for example, classification and regression trees), Bayesian models (such as, for example, Naive Bayes), clustering models (such as, for example, k-means clustering), association rule learning models (such as, for example, a-priori models), artificial neural network models (such as, for example, Perceptron), deep learning models (such as, for example, Deep Boltzmann Machine, or deep neural network), dimensionality reduction models (such as, for example, Principal Component Analysis), ensemble models (such as, for example, Stacked Generalization), and/or other machine learning models. One or more machine learning models can be used for barcode decoding, perturbation tracking, or integrated measurements.

A layer of a neural network (NN), such as a deep neural network (DNN) can apply a linear or non-linear transformation to its input to generate its output. A neural network layer can be a normalization layer, a convolutional layer, a softsign layer, a rectified linear layer, a concatenation layer, a pooling layer, a recurrent layer, an inception-like layer, or any combination thereof. The normalization layer can normalize the brightness of its input to generate its output with, for example, L2 normalization. The normalization layer can, for example, normalize the brightness of a plurality of images with respect to one another at once to generate a plurality of normalized images as its output. Non-limiting examples of methods for normalizing brightness include local contrast normalization (LCN) or local response normalization (LRN). Local contrast normalization can normalize the contrast of an image non-linearly by normalizing local regions of the image on a per pixel basis to have a mean of zero and a variance of one (or other values of mean and variance). Local response normalization can normalize an image over local input regions to have a mean of zero and a variance of one (or other values of mean and variance). The normalization layer may speed up the training process.

A convolutional neural network (CNN) can be a NN with one or more convolutional layers, such as, 5, 6, 7, 8, 9, 10, or more. The convolutional layer can apply a set of kernels that convolve its input to generate its output. The softsign layer can apply a softsign function to its input. The softsign function (softsign(x)) can be, for example, $(x/(1+|x|))$. The softsign layer may neglect impact of per-element outliers. The rectified linear layer can be a rectified linear layer unit (ReLU) or a parameterized rectified linear layer unit (PReLU). The ReLU layer can apply a ReLU function to its input to generate its output. The ReLU function ReLU(x) can be, for example, $\max(0, x)$. The PReLU layer can apply a PReLU function to its input to generate its output. The PReLU function PReLU(x) can be, for example, $x$ if $x \geq 0$ and $ax$ if $x<0$, where a is a positive number. The concatenation layer can concatenate its input to generate its output. For example, the concatenation layer can concatenate four 5×5 images to generate one 20×20 image. The pooling layer can apply a pooling function which down samples its input to generate its output. For example, the pooling layer can down sample a 20×20 image into a 10×10 image. Non-limiting examples of the pooling function include maximum pooling, average pooling, or minimum pooling.

At a time point t, the recurrent layer can compute a hidden state s(t), and a recurrent connection can provide the hidden state s(t) at time t to the recurrent layer as an input at a subsequent time point t+1. The recurrent layer can compute its output at time t+1 based on the hidden state s(t) at time t. For example, the recurrent layer can apply the softsign function to the hidden state s(t) at time t to compute its output at time t+1. The hidden state of the recurrent layer at time t+1 has as its input the hidden state s(t) of the recurrent layer at time t. The recurrent layer can compute the hidden state s(t+1) by applying, for example, a ReLU function to its input. The inception-like layer can include one or more of the normalization layer, the convolutional layer, the softsign layer, the rectified linear layer such as the ReLU layer and the PReLU layer, the concatenation layer, the pooling layer, or any combination thereof.

The number of layers in the NN can be different in different implementations. For example, the number of layers in a NN can be 10, 20, 30, 40, or more. For example, the number of layers in the DNN can be 50, 100, 200, or more. The input type of a deep neural network layer can be different in different implementations. For example, a layer can receive the outputs of a number of layers as its input. The input of a layer can include the outputs of five layers. As another example, the input of a layer can include 1% of the layers of the NN. The output of a layer can be the inputs of a number of layers. For example, the output of a layer can be used as the inputs of five layers. As another example, the output of a layer can be used as the inputs of 1% of the layers of the NN.

The input size or the output size of a layer can be quite large. The input size or the output size of a layer can be n×m, where n denotes the width and m denotes the height of the input or the output. For example, n or m can be 11, 21, 31, or more. The channel sizes of the input or the output of a layer can be different in different implementations. For example, the channel size of the input or the output of a layer can be 4, 16, 32, 64, 128, or more. The kernel size of a layer can be different in different implementations. For example, the kernel size can be n×m, where n denotes the width and m denotes the height of the kernel. For example, n or m can be 5, 7, 9, or more. The stride size of a layer can be different in different implementations. For example, the stride size of a deep neural network layer can be 3, 5, 7 or more.

In some embodiments, a NN can refer to a plurality of NNs that together compute an output of the NN. Different NNs of the plurality of NNs can be trained for different tasks. A processor (e.g., a processor of the computing system 100 descried with reference to FIG. 1) can compute outputs of NNs of the plurality of NNs to determine an output of the NN. For example, an output of a NN of the plurality of NNs can include a likelihood score. The processor can determine the output of the NN including the plurality of NNs based on the likelihood scores of the outputs of different NNs of the plurality of NNs.

Execution Environment

FIG. 1 depicts a general architecture of an example computing device 100 configured to execute the processes and implement the features described herein. The general architecture of the computing device 100 depicted in FIG. 1 includes an arrangement of computer hardware and software components. The computing device 100 may include many more (or fewer) elements than those shown in FIG. 1. It is not necessary, however, that all of these generally conventional elements be shown in order to provide an enabling disclosure. As illustrated, the computing device 100 includes a processing unit 110, a network interface 120, a computer readable medium drive 130, an input/output device interface 140, a display 150, and an input device 160, all of which may communicate with one another by way of a communication bus. The network interface 120 may provide connectivity to one or more networks or computing systems. The processing unit 110 may thus receive information and instructions from other computing systems or services via a network. The processing unit 110 may also communicate to and from memory 170 and further provide output information for an optional display 150 via the input/output device interface 140. The input/output device interface 140 may also accept input from the optional input device 160, such as a keyboard, mouse, digital pen, microphone, touch screen, gesture recognition system, voice recognition system, gamepad, accelerometer, gyroscope, or other input device.

The memory 170 may contain computer program instructions (grouped as modules or components in some embodiments) that the processing unit 110 executes in order to implement one or more embodiments. The memory 170 generally includes RAM, ROM and/or other persistent, auxiliary or non-transitory computer-readable media. The memory 170 may store an operating system 172 that provides computer program instructions for use by the processing unit 110 in the general administration and operation of the computing device 100. The memory 170 may further include computer program instructions and other information for implementing aspects of the present disclosure.

For example, in one embodiment, the memory 170 includes a barcode decoding module 174 for decoding or determining spatial optical barcodes. The memory 170 may additionally or alternatively include a perturbation tracking module 176 for determining perturbations. The memory 170 may additionally or alternatively include an integrated measurements module 178 for performing integrated measurements (such as determining genotype-phenotype or perturbation-phenotype correlations based on the processes shown in FIGS. 2, 3, 6, 7, 11A, and 11B). In addition, memory 170 may include or communicate with the data store 190 and/or one or more other data stores that store images captured, received, or processed, barcodes and perturbations determined, and genotype-phenotype correlations determined.

EXAMPLES

Some aspects of the embodiments discussed above are disclosed in further detail in the following examples, which are not in any way intended to limit the scope of the present disclosure.

Example 1

Deep Learning Enabled Spatial Optical Barcodes for Pooled Library Screens

Genetic and chemical library screens are effective means of achieving high throughput testing of multiple experimental perturbations. These types of experiments, such as CRISPR/Cas9 library screens, have shed light on many biological systems and have led to several important findings in cell systems and drug discovery. Typically, these types of experiments are performed in either arrayed or pooled fashions. Arrayed screens, where individual populations of cells all receive single perturbations, allow for straightforward differentiation of the effects of each experimental condition but often lack the throughput necessary to easily test whole libraries. Since the perturbations are applied to separate populations cells, these screens can be paired with most biological measurements such as genomics or imaging.

Pooled screens, where the complete library of perturbations is applied to single population of cells, allow for higher experimental throughput but generate a large amount of data that require specialized techniques to match each cell with an individual perturbation. Usually these pooled screens rely on unique DNA and RNA sequence, or barcodes, to code for the perturbation given to each individual cell in the population. As such, the outputs in these DNA barcoded pooled screens are genomics based and can be analyzed using next-generation sequencing (NGS) and bioinformatics post-processing. Due to the nature of genetic sequencing, phenotypic information beyond gene expression of individual cells in the pooled screens cannot be retained, making a majority of the existing biological assays impossible to perform in combination with this technique. Currently, there are only a few existing technologies tackling this issue and most are technically challenging to perform, requiring special equipment and many sequential imaging and wash steps to complete, ultimately limiting their utility and throughput.

Summary

This example describes methods for creating, implementing, and analyzing spatial optical barcodes for reading out pooled library screens while preserving cell identity and phenotype. These methods include the barcoding schemes using fluorescence labeled subcellular compartments and the deep learning framework used to analyze experimental results and decode the resulting barcodes.

The example addresses the challenges of encoding and decoding pooled library screens with single-cell resolution while retaining spatial and temporal cellular phenotypes. The invention is comprised of methods to label fluorescent subcellular compartment barcodes as well as methods to combine these barcodes with genetic or chemical perturbation libraries. The invention also includes methods to read-out each barcode using a single round of staining and imaging. This invention describes both the use of epitope tags and fluorescent antibodies as well as clustered regularly interspaced short palindromic repeats (CRISPR) display and RNA fluorescence in situ Hybridization (FISH) probes as individual barcoding schemes. Both methods can use microscopy and deep learning in order to decode and register perturbations with phenotypic measurements.

Deep Learning Enabled Spatial Optical Barcodes for Pooled Library Screens

FIG. 2 illustrates the usage of a pooled library screen. To incorporate phenotypic measurements, pooled library screens can include accurate mapping of each cell to its specific perturbation. Cells can be modified with a unique perturbation and corresponding barcode that can be used to match individual cells to their respective perturbation. Experimental conditions can be applied to the perturbed cell population prior to data collection. Once all of the data has been collected, cells can undergo a single round of fluorescence labeling prior to a final round of imaging. The resulting images and data can be analyzed using deep learning to isolate single cell measurements and corresponding perturbation. An example workflow of deep learning enabled spatial optical barcoding for pooled library screens is shown in FIG. 3.

FIGS. 4A, 4B1, and 4B2 describe two approaches to creating a spatial optical barcode by labeling of unique subcellular locations (or compartments or regions) with multiple fluorescent markers (colors). Fluorescently tagging of repetitive genomic DNA sequences and/or specific subcellular organelles can be performed. Labeling repetitive genomic DNA sequences can employ CRISPR display and single molecule FISH technologies. CRISPR display uses inactivated or dead Cas9 (dCas9) to target guide RNAs (gRNAs) to the nuclear DNA where large areas of repeated DNA sequences are located, such as telomeres and centromeres. The gRNAs used can have modified scaffolds or include tails that can be the target of various fluorescent molecules, such as GFP-tagged MS2 or fluorescently labeled DNA probes used in single molecule FISH. Similarly, subcellular compartments such as mitochondria and the nuclear envelope can be targeted by known sequences of amino acids and artificial protein epitopes, such as human influenza hemagglutinin (HA) and FLAG (for example, having the sequence motif DYKDDDDK). These artificial protein epitope-tagged subcellular compartments can then be targeted with fluorescent antibodies specific for each protein epitope. By creating multiple combinations of compartments and fluorescent colors in each of these labeling schemes we can achieve up to $2^{(number\ of\ compartments \times number\ of\ epitopes)}$ unique barcodes.

FIG. 5 describes combinatorically assembling each barcoding component with a perturbation. Assembling can be performed by combining all barcoding components and perturbations onto magnetic beads and assembling all pieces using molecular biology into a functional plasmid containing a single barcode and perturbation. To prevent crosstalk between the different barcodes and perturbations, an emulsion or partition can be made such that each droplet contains all the necessary reagents and DNA necessary to create each barcoded perturbation plasmid. Cells can also be introduced in this emulsion step to ensure that only single perturbations enter each cell.

These barcoding experiments can be read and decoded using deep learning. Classifying each cell in the resulting images can be difficult and time consuming especially at the single-cell level. To reach the necessary throughput to analyze pooled screens, these steps can be performed by a deep learning model to find, analyze, and decode each cell in a pooled library screen with spatial optical barcodes. FIG. 6 describes a typical workflow for the deep learning analysis of these experiments. The inputs can be experimental data (e.g., morphology or live cell imaging) and images of all cells with fluorescent barcodes. The outputs can be a set of single cell phenotype measurements and their associated perturbations.

This example describes high throughput library screens coupled with multiplexed phenotypic measurements that have previously been impossible to observe simultaneously. High throughput library screens coupled with multiplexed phenotypic measurements can be used for applications such as drug development and personalized medicine.

Example 2

Integrating Heterogeneous Measurements in Single Cells with Spatial Genomics and Deep Learning Advances in imaging and genomics have enabled a shift away from a population level understanding of living systems towards one at the single-cell level. In concert with these advances in measurement technologies, advances in machine learning methods and their associated hardware accelerators have kept pace with the need to extract insights from these large, single-cell datasets. Together these advances are making performing integrated measurements, in which multiple facets of cellular state are measured within a single cell, possible. This type of experiment has opened new avenues of investigation into previously intractable questions. For example, how cells use signaling dynamics to encode information about a stimulus and then decode dynamics to produce a transcriptional response remains poorly understood. This problem has been challenging because differences in cell state mean signaling dynamics can vary significantly between cells, even when the stimulus is identical. To investigate how cells process and encode information through signaling dynamics, an experiment measures the input (stimulus), the encoding (signaling dynamics) and, the output (gene expression), all in the same cell. One such experimental demonstration of integrated measurements uses microfluidics to connect live-cell imaging with single-cell RNA-Sequencing (scRNA-Seq) to answer this question, for example, for NF-κB and the TLR4 pathways.

While integrated measurements have been realized, existing approaches are difficult to perform for large numbers of cells. Moreover, to be used for biological discovery, integrated measurements should be performed in the setting of unbiased genetic perturbations, to fully test the impact that each piece of the system has on the whole (e.g., the impact of a single node has on information transmission for the whole signaling pathway). While pooled CRISPR libraries offer a powerful and cost-effective way to test thousands of perturbations simultaneously, using pooled CRISPR libraries with integrated measurements involves imaging the cells. Using pooled CRISPR libraries with integrated measurements which involves imaging the cells can be challenging because of the need to match cells with the perturbations the cells have received without using sequencing. Methods that use optical barcodes, genetic sequences that can be identified with imaging, can be used. However, such methods can be limited by either their technical difficulty or their sample throughput.

This example describes combining deep learning with spatial genomics to create a scalable technological platform for performing imaging-based integrated measurements on pooled CRISPR libraries. By coupling live-cell imaging with end-point sequential FISH (seqFISH), integrated single-cell records of signaling dynamics and gene expression at $10^2$ loci in over $10^5$ cells can be routinely collected. This example describes an integrated pipeline of deep learning modules to automate the analysis of these experiments. This example describes a new approach to imaging pooled CRISPR screens, which includes creating new optical barcodes that only require one to two rounds of imaging, can be easily interpreted with deep learning, and have a coding space sufficient for genome-wide screens. Using the technologies described in this example, pathways can be studied, for example, to identify feedback loops and signaling that gives rise to dynamics in pathways, and to determine the impact these dynamics have on gene expression.

1. A Deep Learning Pipeline for Processing Integrated Measurement Data to Extract Single-Cell Records Rationale Advances in computational software and hardware have made deep learning a powerful tool for analyzing large sets of microscopy images. Development of annotated training datasets has led to deep learning models that can accurately perform tasks including image classification, segmentation, and object tracking (Moen et al., Deep learning for cellular image analysis. Nat Methods 16, 1233-1246 (2019). https://doi.org/10.1038/s41592-019-0403-1, the content of which is incorporated herein by reference in its entirety). The coinciding emergence of inexpensive cloud computing providers has made deep learning methods more accessible, as it allows users on-demand access to specialized hardware like GPUs. Additionally, cloud computing has made it possible to massively parallelize data processing, which significantly reduces the time required to analyze large datasets. All told, these advances will enable automation of key analysis steps for biological imaging experiments.

This type of automation can be critical to the practical implementation of the previously mentioned integrated measurement experiments. Thus far, the challenge imposed by cellular image analysis has been a barrier to this becoming a widespread approach. This analysis step is necessary to extract features like signaling dynamics and gene expression for each cell.

Approach

A system for cloud-based model deployment called the DeepCell Kiosk has been developed (Bannon et al., Dynamic allocation of computational resources for deep learning-enabled cellular image analysis with Kubernetes. bioRxiv 505032; doi: doi.org/10.1101/505032, the content of which is incorporated herein by reference in its entirety). The DeepCell Kiosk uses Kubernetes to dynamically manage a cloud-based compute cluster for high-throughput data processing that ultimately minimizes time and expense. Deep learning models are hosted by dedicated model servers with access to GPU resources for predictions. Other compute tasks that do not require a GPU, such as pre- and post-processing, are located on CPU nodes. This framework ensures that the more expensive resources (GPUs) are only used when necessary. Additionally, the Kiosk obeys a set of resource management guidelines to dynamically scale the number of compute nodes available in the cluster in response to the size of data processing tasks. This framework enables massively parallel data processing such that we can process 100,000 megapixel images in 90 minutes for only $30. When data is uploaded to the Kiosk for processing, it is managed by a "consumer" that orchestrates sending data to the appropriate model and performs any pre- and post-processing tasks. For example, an application-specific consumer can send data to four different models to complete processing. An integrated measurements consumer can direct each data type to the appropriate model for processing before extracting single-cell feature sets. Nuclear and cytoplasmic segmentation and cell tracking models have been developed (Moen et al., Accurate cell tracking and lineage construction in live-cell imaging experiments with deep learning. bioRxiv 803205; doi: doi.org/10.1101/803205; U.S. patent application Ser. No. 16/859,885, entitled TRACKING BIOLOGICAL OBJECTS OVER TIME AND SPACE, filed Apr. 27, 2020; the content of each of which is incorporated herein by reference in its entirety) and can implement object-based error detection. This new approach for assessing model performance can enable specifically refining models to eliminate biologically relevant errors. Deep learning models can be used for spot detection and FISH analysis.

Figure 7:
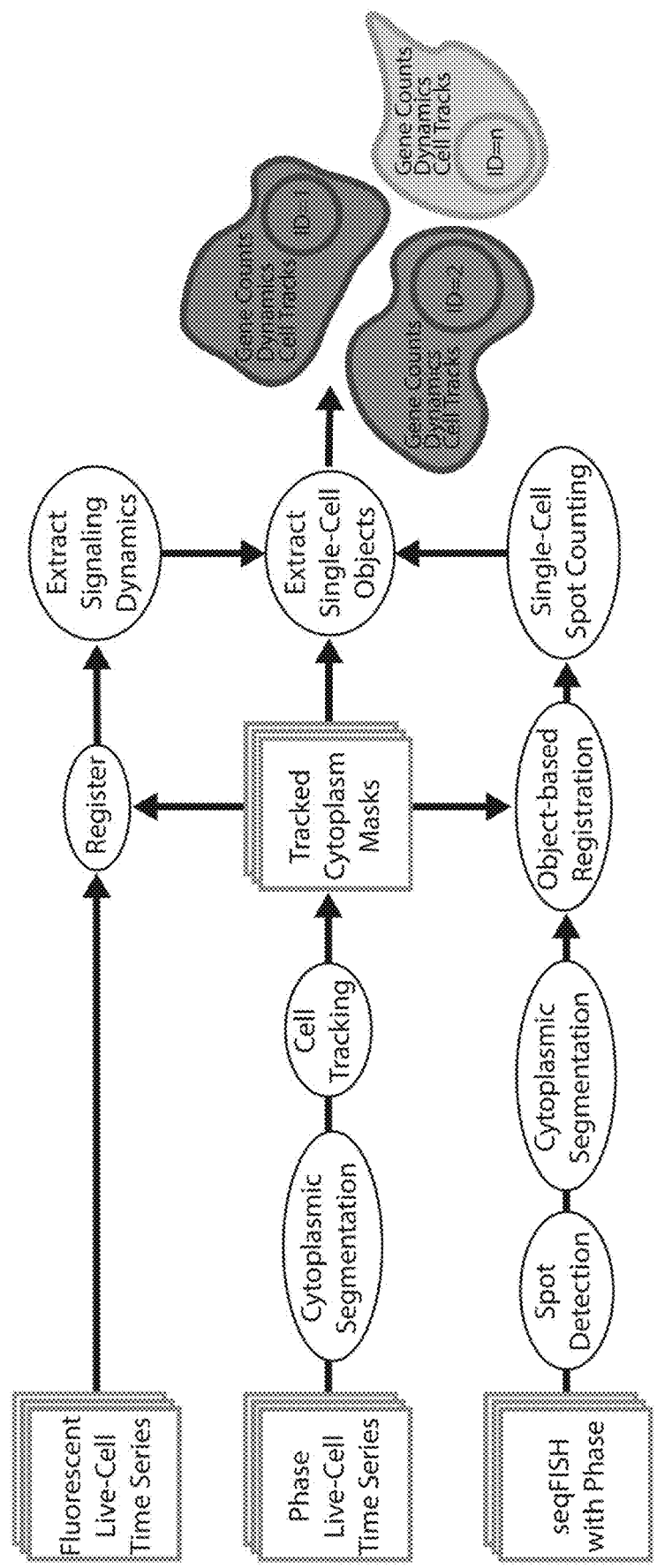
FIG. 7. An example integrated measurement data processing pipeline.

FIG. 7. An example integrated measurement data processing pipeline. The phase live-cell imaging channel can be used for cytoplasmic segmentation and cell tracking. The cell IDs assigned in the last frame of live imaging can be used to construct the final set of single-cell data objects. Next, the fluorescent time series data can be matched to the tracked cytoplasm data and signaling dynamics can be measured for each cell. Then, the seqFISH dataset can be run through a spot detection model. The phase channel collected during seqFISH imaging can undergo cytoplasmic segmentation such that the cell objects identified can be registered to the live cell objects. Once this correspondence is established, gene counts can be tallied for each cell. Finally, single-cell data objects can be constructed with each cell's movements, signaling dynamics and gene counts.

Results

The proposed pipeline for integrated measurements can enable the rapid processing of several disconnected datasets into a set of single-cell data objects. By utilizing the Deepcell Kiosk, several GPU nodes each processing 5-10 megapixel images per second can be run. With appropriate scaling of GPU nodes, the ability to rapidly process data is limited only by upload speed (for example, about 200 images per second). An example implementation of the data processing pipeline is shown in FIG. 7. The raw input to the pipeline can be live-cell imaging data and end-point seqFISH data. In these experiments, live-cell imaging can collect a phase channel for cell tracking and a fluorescent channel reporting signaling dynamics. After imaging, cells can be fixed and undergo several rounds of seqFISH to measure gene expression of a panel of genes. The integrated measurements cloud pipeline can receive a zipped file of the three datasets and return single-cell data objects. Within the cluster created by the DeepCell Kiosk, the integrated measurements pipeline can run each processing task in parallel. Where appropriate, the integrated measurements pipeline can also break the dataset into smaller chunks that can also be processed in parallel.

2. A Complete Methodological Toolkit for Integrated Measurement Perturbation Screens of Live, Mammalian Cells Rationale CRISPR-Cas9 screens have proven to be a powerful next-generation tool for discovering new biology. These screens are most commonly used in selection assays or scRNA-Seq measurements. In each case, a DNA barcode is present to identify guide RNAs at either the population or single-cell level during end point sequencing. Imaging pooled libraries can be difficult because which gRNA each cell received must be identified. However, imaging is needed for the goal of pairing reverse genetics with integrated measurements. New methods have connected imaging with pooled CRISPR screens by introducing a unique barcode sequence to each gRNA that can be read out using the microscope. While innovative, these methods are challenging to use in practice, as they either require difficult amplification steps or have limited throughput (e.g. imaging at 100× magnification).

Approach

This example shows a set of spatial optical barcodes can be designed and processed with a single round of staining and imaging. The example also shows a complementary method for library assembly that utilizes cost-saving pooled oligonucleotide synthesis while retaining the ability to customize plasmid design.

2a. Optical Barcodes for High-Throughput Microscopy Screening of CRISPR Libraries in Live Mammalian Cells Rationale Optical barcodes have proven to be useful for the application of pooled CRISPR screens to phenotypes that can only be captured using imaging. However, new methods are needed to make these approaches accessible to the life-science community. Current methods for barcoding mammalian cells rely on multiple rounds of staining and imaging using either FISH or in situ sequencing. Both methods utilize 12-digit barcodes that require up to 18 rounds of staining and imaging. While the precise details of the protocols vary, each round of staining includes multiple washes and incubations prior to imaging. While staining times can potentially be reduced with robotic assistance, the time spent on the microscope is governed by the number of staining rounds required to read out the barcodes and the magnification needed to image the barcodes. While FISH-based barcodes are imaged at 100×, in situ sequencing barcodes can be imaged at 10×, which drastically reduces the total imaging time. However, this advantage relies on a difficult amplification procedure that has prohibited widespread adoption. For many laboratories, microscope availability becomes the limiting factor that bottlenecks the total productivity of the laboratories. Given this constraint, a barcoding method that utilizes a single round of staining increases the throughput of these screens by at least 10-fold. An alternative approach to sequential barcodes creates optical barcodes by labeling spatially distinguishable compartments in the cell. For example, these spatial barcodes can be cellular organelles labeled with fluorescent proteins. With this design, the number of possible barcodes is $2^{(\#colors) \times (\#compartments)} - 1$ which can cover a library of over 1000 perturbations with only three colors and four compartments.

Approach

A spatial barcode scheme for use in mammalian cells was developed. Instead of labeling organelles as distinct spatial domains, CRISPR-Display and RNA FISH were used to label repetitive regions (e.g. telomeres and centromeres) in the nucleus to create distinct spatial patterns. CRISPR-Display uses a gRNA against a repetitive sequence to direct dCas9 to stably bind to that region. Typical implementations use fluorescent proteins bound to dCas9 and fluorescent oligos to label optical detection probe binding sites that introduced into the gRNA scaffold. The CRISPR-Display design was modified to use an unlabeled dCas9 and instead optical detection probe binding sites in the gRNA scaffold can be labeled with fluorescent oligos (FIG. 8B1). In order to image CRISPR-Display barcodes at lower magnification (e.g. 20× or 40×), FISH labeling signal can be amplified using signal amplification by exchange reaction by substituting single fluorescent probes with concatamer probes as shown in FIG. 8B2 (FIG. 8B2). This method enables synthesis of long amplification probes with many FISH optical detection probe binding sites in vitro and then directly amplifying signal in cells without any additional reactions.

FIGS. 8A, 8B1, 8B2, and 8C-8F. CRISPR-Display for spatial barcoding. FIG. 8A. Optical barcoding screens was performed in a dCas9 background that serves to induce the knockdown specified by the ΔgRNA and to label repetitive regions according to barcode gRNAs. FIG. 8B1. The CRISPR-Display technique uses dCas9 to stably bind to regions of the genome specified by the guide. In this example, the scaffold was modified to include a "FISH" tail with up to three optical detection probe binding sites for fluorescent oligonucleotides. Barcode signal can be amplified by substituting single fluorescent probes with concatamer probes as shown in FIG. 8B2. FIGS. 8C-8D. gRNAs targeted against repetitive regions of the genome produced distinct patterns in the nucleus (FIG. 8D). FIG. 8E. A deep learning classifier that accurately distinguished between these patterns was constructed. The deep learning barcode classifier can be trained using training dataset of cells labeled with multiple compartments in different channels. Alternatively or additionally, the deep learning barcode classifier can be trained using training dataset of cells labeled with multiple compartments in the same channel. FIG. 8F. Genetic knockdowns using CRISPR-dCas9.

Cas9 Endonuclease Dead, also known as dead Cas9 or dCas9, is a mutant form of Cas9 whose endonuclease activity is removed through point mutations in its endonuclease domains. Similar to its unmutated form, dCas9 is used in CRISPR systems along with gRNAs to target specific genes or nucleotides complementary to the gRNA with PAM sequences that allow Cas9 to bind. Cas9 ordinarily has 2 endonuclease domains called the RuvC and HNH domains. The point mutations D10A and H840A change two important residues for endonuclease activity that ultimately results in its deactivation. Although dCas9 lacks endonuclease activity, it is still capable of binding to its guide RNA and the DNA strand that is being targeted because such binding is managed by other domains. This alone is often enough to attenuate if not outright block transcription of the targeted gene if the gRNA positions dCas9 in a way that prevents transcriptional factors and RNA polymerase from accessing the DNA. However, this ability to bind DNA can also be exploited for activation since dCas9 has modifiable regions, typically the N and C terminus of the protein, that can be used to attach transcriptional activators.

Assignment of a perturbation to a cell is possible if each cells receives at most one barcoded plasmid. During lentiviral delivery of the perturbation library to cells, a two-part approach can be implemented to ensure that each cell receives only one perturbation. First, the concentration of the virus can be titrated to achieve a multiplicity of infection (MOI) of 0.5, which reduces the probability of double infection. Additionally, a specific subset of barcodes that enable detection of any double infections can be selected (FIG. 9). For example, in a barcode with n colors and m compartments, there are n×m barcode subunits. If barcodes are restricted such that only $$\frac{n \times m}{2}$$

subunits are used in each barcode, any cell that appears with more subunits is the result of a double infection and can be excluded during post-processing. This design restricts the number of possible barcodes to $$\frac{(n \times m)!}{\left(\frac{n \times m}{2}\right)! \left(\frac{n \times m}{2}\right)!}.$$

FIG. 9. An error detection scheme for identifying multiple infections. With three colors and four spatial compartments, $2^{3 \times 4} = 4096$ barcodes are possible. Each barcode has twelve possible barcode subunits each being a combination of one of the three colors and one of the four spatial compartments. For error detection, only six-subunit barcodes can be used such that any cell infected with two barcodes have more than six subunits and can be rejected. There are $$\frac{12!}{6!6!} = 924$$

possible six-subunit barcodes.
Results

This example shows gRNAs against three repetitive regions were tested: α satellite, β satellite, and telomeres (Table 1). Experiments demonstrated that these guides label distinct compartments that are accurately identified by a deep learning classifier (FIG. 8E). Additionally, the modified gRNA scaffold design was tested to show that the modified gRNA scaffold design can be used for FISH labeling. With these three compartments (e.g., α, β, and telomere) and three fluorescent probes (e.g., green, red, and far-red), a library of $2^{3 \times 3} = 512$ barcodes can be constructed. If the error detection scheme described in this example is implemented, the number of available barcodes is reduced to 126.

TABLE 1

| gRNA sequences for spatial compartments. | |
| --- | --- |
| Compartment | Sequence |
| α satellite | 5'-GAATCTGCAAGTGGATATT-3' (SEQ ID NO: 1) |
| β satellite | 5'-AGGTGATGTAACTCTTGTCT-3' (SEQ ID NO: 2) |
| Telomere | 5'-GTTAGGGTTAGGGTTAGGGTTA-3' (SEQ ID NO: 3) |

In order to expand the possible library size, a fourth compartment or color can be used. The framework used to test gRNAs can rely on staining fixed cells with dCas9 pre-complexed to gRNA. This method has enabled rapid testing of gRNA designs. Alternatively or additionally, a lentiviral delivery system can be used.

Since microscope availability is one of the major limitations of currently available methods, the approximate microscopy time required for the approach described in this example was analyzed. Ultimately, the number of cells that can be analyzed in a single experiment is determined by the live imaging conditions. For example, for studying the signaling dynamics of interest, these signals can be imaged at 20× with five minute intervals. Under these conditions, a microscope can image approximately 60,000 cells (Table 2a). Live imaging throughput could be improved by using a lower magnification or extending the duration of the imaging interval. A library of 384 barcodes targeted against 100 genes can be used (Table 2b). With these parameters, two live imaging replicates can require image 120,000 cells (Table 2c). Assuming a MOI of 0.5, about 150 cells per gRNA are expected. Given the live imaging conditions described, two replicates can be collected in order to complete this experiment and image a sufficient number of cells. Finally, the most time-intensive step in this approach is the end-point measurement of gene expression (Table 2d). Traditionally seqFISH has required high magnification to achieve single molecule resolution. Methods for signal amplification can enable lower magnification and faster imaging collection in order to reduce imaging time.

TABLE 2

| Scalability of optical barcoding experiments in a 96-well plate | |
| --- | --- |
| a) Live Imaging at 20x | |
| 3 | Wells per 5 minutes collection |
| 26 | Tiled FOV per well |
| 800 | Cells per FOV |
| 62,400 | Total Cells |
| b) Library Design | |
| 100 | Total genes with 3 guides per gene |
| 3 | gRNAs per gene |

TABLE 2-continued

| Scalability of optical barcoding experiments in a 96-well plate | |
|---|---|
| 84 | Nonsense control gRNAs |
| 384 | Total plasmids/gRNAs |
| | c) Imaging Depth |
| 0.5 | Multiplicity of infection |
| 150 | Cells per gRNA |
| 115,200 | Total cells per experiment |
| | d) Imaging at 60x |
| 234 | Tiled FOV per well |
| 1 | Minutes per FOV |
| 3.9 | Hours per well |
| 11.7 | Total hours |

2b. Pooled Assembly of Pre-Designed Multi-Part Plasmids

Rationale

This section of the example describes a method of assembling pools of pre-specified combinatorial plasmids whose components are too large to directly synthesize. This method can enable multiplexed or blanketing perturbation screens in which each plasmid delivers several different programmable perturbations to a single cell. For example, in order to assemble the library proposed in section 2a, three barcode gRNAs can be combined with one perturbation gRNA. Current assembly methods that support directed assignment of specific sequence combinations are limited to a total sequence length of approximately 300. Alternatively or additionally, methods such as Golden Gate Shuffling that enable combining multiple large (200 bps) fragments are limited to random assembly.

An alternative approach is to synthesize specific plasmids while retaining the advantages of pooled synthesis. This method uses oligonucleotide-baited beads to sequester oligonucleotides with the corresponding bait sequence from a pooled library. Individual beads are then isolated in emulsion droplets where the sequestered sequences can be assembled into a complete plasmid. However, this method is limited to components that can be synthesized within the constraints of an oligonucleotide pool, which precludes its application to the assembly of larger components.

Approach

The bead-based assembly method can be leveraged to facilitate pooled library assembly. Oligonucleotide-baited beads can be used to sequester pooled plasmid components that can then labeled with matching oligonucleotide sequences. The set of 384 oligonucleotide bait sequences (also referred to herein as bead codes) can enable directed assembly of 384 unique plasmids in a single pooled reaction. Once prey sequences have annealed to the oligonucleotide-baited beads, individual beads can be isolated in separate droplets in an emulsion. Within each droplet, the prey sequences sequestered by the bead can be assembled into a complete plasmid based on pre-designed regions of homology (FIG. 10F). Finally, the emulsion can be broken to release the completed plasmids into a pool where the plasmids can be purified and used for downstream assembly.

To create the optical barcode library described in section 2a, plasmids can be built off of a lentivirus destination vector with a selection cassette designed for mammalian cell culture. To assemble spatial barcodes, a set of modular barcode subunits each composed of the U6 promoter, a compartment-specific gRNA, the plasmid scaffold, and a set of FISH optical detection probe binding sites can be created (FIG. 10A). Each spatial compartment can have 8 possible subunit versions depending on the combination of FISH optical detection probe binding sites included in the gRNA tail. Each assembled plasmid can include one subunit version for each spatial compartment in addition to a perturbation-specific gRNA sequence under a U6 promoter (FIG. 10E).

The design of specific library sequences can be performed in Python leveraging the BioPython package. While each round of synthesis may be limited to 384 unique plasmids, multiple pools from different rounds of synthesis can be combined for experimental use as long as distinct spatial barcodes were used for each subpool. Computationally, each bead code sequence can be assigned to a unique spatial barcode and perturbation gRNA. Given a final list of bead codes and barcode subunit combinations, a robot can populate a 384 well plate with the specified combinations of bead codes and barcode subunits. After each bead code has been enzymatically attached to each barcode subunit in the well, the components of this reaction can be pooled and used for plasmid assembly (FIG. 10B).

The final stage of plasmid assembly can combine three sets of pooled components: baited-beads, pooled gRNA oligos, and barcode subunits. Oligonucleotide-baited beads can be prepared (FIG. 10D). The barcode subunit pool can be prepared as described above. Finally, the perturbation gRNA sequences can be synthesized as a pool, with the preassigned bead code included in the synthesis (FIG. 10C). After combining the three pools and facilitating oligonucleotide annealing, the creation of an emulsion can isolate each individual bead in a droplet containing the destination plasmid backbone and other assembly reagents. Assembly can, for example, leverage Golden Gate cloning and a set of optimized overhangs to combine each of the four inserts into the backbone in a prespecified order (FIG. 10F). Finally, after breaking the emulsion, the resulting plasmid pool can be purified for downstream applications.

FIGS. 10A-10E. Exemplary components for assembling a library of barcoded plasmids. FIG. 10A. Each barcode subunit can include of a U6 promoter, a compartment gRNA and a set of FISH optical detection probe binding sites. For each compartment, there can be 8 subunit versions corresponding to $2^3$ possible color combinations. FIG. 10B. A set of unique oligonucleotide sequences (bead codes) can be used to identify the components of each unique final plasmid. These oligonucleotides can be attached to barcode subunits in an arrayed reaction. FIG. 10C. The perturbation (Δ) gRNAs that form the basis of a screen can be ordered in a pool with each gRNA associated with a bead code. FIG. 10D. Additionally, a corresponding set of beads can be prepared each labeled with one bead code. FIG. 10E. In the final reaction, beads can pull down their corresponding barcode subunits and ΔgRNA before a reaction (e.g., a Golden Gate reaction) to assemble the final plasmid in a lentivirus backbone. FIG. 10F. Library sequence designs.

Results

Each successive step in the assembly protocol can be performed in small arrayed reactions or in pooled reactions. The correct output size of each reaction can be confirmed. Golden Gate cloning can be used for multi-part assembly. The assembling method described in this section is also compatible with PCR-based assembly methods such as Gibson Assembly. Following the completion of pooled assembly reactions, the plasmid inserts can be sequenced to verify correct assembly and to measure the prevalence of any errors. The efficacy of the design for lentiviral delivery can be determined by sequencing the DNA integrated into transduced cells. This experiment can enable identification of any possible problems caused by the presence of repetitive sequences (U6 promoter and gRNA scaffolds) during lentiviral packaging. Alternatively or additionally, plasmid can be designed to reduce recombination and polycistronic designs in which a single Pol III promoter expresses multiple gRNAs later separated by the endogenous tRNA processing system. In any form, this approach to library assembly can extend beyond the application described in section 2a and can be used to deliver multiple gRNA perturbations with a single plasmid. While other assembly methods exist for multiplexing, they all rely on the assembly of isolated gRNA sequences and cannot take advantage of the time and cost-saving measures of pooled oligonucleotide synthesis.

3. Integrated Measurement Experiment

FIG. 11A. Experimental workflow for an integrated measurement experiment. Cells (e.g., RAW 264.7 cells) expressing dCas9 can be transduced with a barcoded, perturbation library. After selection, live imaging can collect data about signaling dynamics of interest following activation. Next, cells can be fixed and then stained for several rounds of seqFISH. Finally, cells can be be stained to reveal their optical barcode. The resulting data can be processed using the pipeline described in FIG. 7 with the addition of a barcode classifier to match each cell to its gRNA perturbation. FIG. 11B. Experimental workflow for an integrated measurement experiment.

ADDITIONAL CONSIDERATIONS

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Accordingly, phrases such as "a device configured to" are intended to include one or more recited devices. Such one or more recited devices can also be collectively configured to carry out the stated recitations. For example, "a processor configured to carry out recitations A, B and C can include a first processor configured to carry out recitation A and working in conjunction with a second processor configured to carry out recitations B and C. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for determining perturbations in a plurality of single cells, the method comprising:
expressing in each of a plurality of single cells (i) a plurality of guide ribonucleic acids (gRNAs) comprising a perturbation gRNA (AgRNA) and one or more barcode gRNAs, and (ii) a dead CRISPR associated protein 9 (dCas9), wherein the barcode gRNAs each comprises a barcode region comprising one or more optical detection probe binding sites for a plurality of optical detection probes, thereby the AgRNA binds to a first dCas9 and the first dCas9 bound to the AgRNA binds to a chromosome sequence of a genome of a single cell, resulting in a perturbation in the single cell, and thereby each of the barcode gRNAs binds to a second dCas9 and the second dCas9 bound to the barcode gRNA binds a predetermined spatial region of the genome of the single cell, wherein presence of a combination, of (i) each of the optical detection probe binding sites in the barcode regions of the barcode gRNAs expressed in the single cell and (ii) the corresponding predetermined spatial region where the second dCas9 bound to the barcode gRNA comprising the barcode region binds to, indicates the AgRNA is expressed in the single cell;
staining the plurality of single cells with the plurality of optical detection probes, wherein two optical detection probes of the plurality of optical detection probes comprise different optical labels and are capable of binding to two optical detection probe binding sites, of the barcode gRNAs expressed in the plurality of single cells, comprising different sequences, thereby optical detection probes of the plurality of optical barcodes bind to the optical detection probe binding sites of the barcode gRNAs expressed in the plurality of single cells;
imaging the plurality of single cells comprising the optical detection probes bound to the optical detection probe binding sites of the barcode gRNAs expressed in the plurality of single cells to generate a plurality of images; and
analyzing the plurality of images generated to determine, for each of the plurality of single cells, the combination of optical detection probe binding sites expressed in the single cell and corresponding predetermined spatial regions, thereby determining the perturbation in the single cell.

2. The method of claim 1, wherein each of the plurality of gRNAs comprises from 5' to 3' a guide region and a scaffold region.

3. The method of claim 2, wherein the scaffold region comprises the barcode region.

4. The method of claim 1, wherein the barcode region is on the 3' end of the gRNA.

5. The method of claim 1, wherein each of the plurality of gRNAs comprises two or more ΔgRNAs.

6. The method of claim 5, thereby each of the two or more ΔgRNAs binds to a first dCas9 and the first dCas9 bound to the AgRNA binds to a chromosome sequence of the genome of the single cell, resulting in a perturbation in the single cell.

7. The method of claim 1, wherein the chromosome sequence of the genome of the single cell the first dCas9 bound to the ΔgRNA binds to is predetermined by a guide region of the ΔgRNA, and wherein the chromosome sequence of the genome of the single cell the first dCas9 bound to the ΔgRNA binds to is a reverse complement of a sequence of the guide region of the ΔgRNA.

8. The method of claim 1, wherein the chromosome sequence of the genome of the single cell comprises a gene of interest.

9. The method of claim 1, wherein the predetermined spatial region of the genome of the single cell comprises a repetitive region of the genome of the single cell and/or comprises a repetitive region of each chromosome of the genome of the single cell.

10. The method of claim 1, wherein the predetermined spatial region of the genome of the single cell comprises a telomere, an alpha satellite, a beta satellite of each chromosome of the genome of the single cell.

11. The method of claim 1, wherein the predetermined spatial region of the genome of the single cell that the second dCas9 bound to the barcode gRNA binds to is predetermined by a guide region of the barcode gRNA.

12. The method of claim 1, wherein the barcode region of a barcode gRNA comprises at least three optical detection probe binding sites.

13. The method of claim 1, wherein the barcode region of a barcode gRNA comprises presence or absence of each of at least three possible optical detection probe binding sites.

14. The method of claim 1, wherein a combination of an optical detection probe binding site expressed in each of the plurality of single cells and the corresponding predetermined spatial region represents a barcode subunit, wherein the combination of optical detection probe binding sites expressed in each of the plurality of single cells and the corresponding predetermined spatial regions represents a barcode comprising a plurality of barcode subunits, and wherein each of the plurality of barcode subunits is selected from a plurality of possible barcode subunits.

15. The method of claim 14, wherein the barcode comprises fewer than all of the plurality of possible barcode subunits.

16. The method of claim 15, wherein presence of any of the remaining of the plurality of possible barcode subunits in the barcode indicates an error has occurred.

17. The method of claim 15, comprising performing error detection using the remaining of the plurality of possible barcode subunits.

18. The method of claim 1, wherein the number of the plurality of possible barcodes is at least 1000, and/or wherein a number of the perturbations is at least 1000.

19. The method of claim 1, wherein the plurality of gRNAs is under transcription control of a promoter, wherein two or more of the plurality of gRNAs is under control of a promoter, or wherein each of the plurality of gRNAs is under control of a promoter.

20. The method of claim 1, wherein analyzing the plurality of images generated comprises: analyzing the plurality of images generated to determine, for each of the plurality of single cells, the combination of optical detection probe binding sites expressed in the single cell and corresponding predetermined spatial regions using at least one machine learning model, thereby determining the perturbation in the single cell.

21. The method of claim 1, wherein the perturbation comprises repression or activation of transcription or repression or activation of replication.

* * * * *